United States Patent
Alimi

(10) Patent No.: US 9,642,876 B2
(45) Date of Patent: *May 9, 2017

(54) METHOD OF PREVENTING OR TREATING SINUSITIS WITH OXIDATIVE REDUCTIVE POTENTIAL WATER SOLUTION

(71) Applicant: Oculus Innovative Sciences, Inc., Petaluma, CA (US)

(72) Inventor: Hojabr Alimi, Santa Rosa, CA (US)

(73) Assignee: SONOMA PHARMACEUTICALS, INC., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,361

(22) Filed: Oct. 27, 2015

(65) Prior Publication Data
US 2016/0045547 A1 Feb. 18, 2016

Related U.S. Application Data

(63) Continuation of application No. 10/916,566, filed on Aug. 11, 2004, now Pat. No. 9,168,318, which is a
(Continued)

(51) Int. Cl.
*A61K 33/00* (2006.01)
*A61K 33/20* (2006.01)
(Continued)

(52) U.S. Cl.
CPC .............. *A61K 33/20* (2013.01); *A01N 59/00* (2013.01); *A61K 9/007* (2013.01); *A61K 9/0014* (2013.01);
(Continued)

(58) Field of Classification Search
CPC ........ A01N 59/00; A61K 33/00; A61K 33/20; A61K 45/06; A61K 47/32; A61K 9/0014;
(Continued)

(56) References Cited

U.S. PATENT DOCUMENTS

| 3,066,095 A | 11/1962 | Hronas |
| 3,616,355 A | 10/1971 | Themy et al. |

(Continued)

FOREIGN PATENT DOCUMENTS

| CN | 1 231 994 A | 10/1999 |
| EP | 0 368 812 A1 | 5/1990 |

(Continued)

OTHER PUBLICATIONS

Allergic rhinitis [online] retrieved on May 26, 2016 from: http://www.webmd.com/allergies/tc/allergic-rhinitis-prevention.*
(Continued)

*Primary Examiner* — Ernst V Arnold
(74) *Attorney, Agent, or Firm* — Leydig, Voit & Mayer, Ltd.

(57) ABSTRACT

Provided is a method for preventing or treating sinusitis by administering a therapeutically effective amount of an oxidative reduction potential (ORP) water solution that is stable for at least about twenty-four hours. The ORP water solution administered in accordance with the invention can be combined with one or more suitable carriers. The ORP water solution can be administered alone or, e.g., in combination with one or more additional therapeutic agents.

19 Claims, 3 Drawing Sheets

Related U.S. Application Data continuation-in-part of application No. 10/862,092, filed on Jun. 4, 2004, now abandoned.

(60) Provisional application No. 60/533,583, filed on Dec. 30, 2003.

(51) Int. Cl.

| | | |
|---|---|---|
| *A61K 45/06* | (2006.01) | |
| *A61K 47/32* | (2006.01) | |
| *A61L 2/22* | (2006.01) | |
| *A01N 59/00* | (2006.01) | |
| *A61K 9/00* | (2006.01) | |
| *A61L 2/00* | (2006.01) | |
| *A61L 2/18* | (2006.01) | |
| *C02F 1/461* | (2006.01) | |
| *C02F 1/467* | (2006.01) | |
| *A61L 2/03* | (2006.01) | |
| *C02F 1/72* | (2006.01) | |
| *C02F 1/76* | (2006.01) | |
| *C02F 103/02* | (2006.01) | |

(52) U.S. Cl.
CPC ............ *A61K 9/0019* (2013.01); *A61K 33/00* (2013.01); *A61K 45/06* (2013.01); *A61K 47/32* (2013.01); *A61L 2/0088* (2013.01); *A61L 2/186* (2013.01); *C02F 1/4618* (2013.01); *C02F 1/4672* (2013.01); *A61L 2/035* (2013.01); *A61L 2/22* (2013.01); *A61L 2202/11* (2013.01); *A61L 2202/122* (2013.01); *A61L 2202/17* (2013.01); *A61L 2202/24* (2013.01); *C02F 1/4674* (2013.01); *C02F 1/722* (2013.01); *C02F 1/76* (2013.01); *C02F 2001/46195* (2013.01); *C02F 2103/026* (2013.01); *C02F 2201/4618* (2013.01); *C02F 2201/46115* (2013.01); *C02F 2209/04* (2013.01); *C02F 2209/06* (2013.01); *C02F 2209/40* (2013.01); *C02F 2303/04* (2013.01)

(58) Field of Classification Search
CPC ... A61K 9/0019; A61K 9/007; A61L 2202/11; A61L 2202/122; A61L 2202/17; A61L 2202/24; A61L 2/0088; A61L 2/035; C02F 1/4674; C02F 1/722; C02F 1/76; C02F 2001/46195; C02F 2103/026; C02F 2201/46115; C02F 2201/4618; C02F 2209/04; C02F 2209/06; C02F 2209/40; C02F 2303/04

See application file for complete search history.

(56) References Cited

U.S. PATENT DOCUMENTS

| | | |
|---|---|---|
| 3,975,246 A | 8/1976 | Eibl et al. |
| 4,048,032 A | 9/1977 | Eibl |
| 4,121,991 A | 10/1978 | Miller et al. |
| 4,236,992 A | 12/1980 | Themy |
| 4,242,446 A | 12/1980 | Madappally et al. |
| 4,289,599 A | 9/1981 | Fushihara |
| 4,296,103 A | 10/1981 | Laso |
| 4,615,937 A | 10/1986 | Bouchette |
| 4,666,621 A | 5/1987 | Clark et al. |
| 4,670,252 A | 6/1987 | Sampathkumar |
| 4,767,511 A | 8/1988 | Aragon |
| 4,781,974 A | 11/1988 | Bouchette et al. |
| 4,979,938 A | 12/1990 | Stephen et al. |
| 5,063,922 A | 11/1991 | Hakkinen |
| 5,079,010 A | 1/1992 | Natterer et al. |
| 5,084,011 A | 1/1992 | Grady |
| 5,244,768 A | 9/1993 | Inaba |
| 5,271,943 A | 12/1993 | Bogart et al. |
| 5,287,847 A | 2/1994 | Piper et al. |
| 5,312,281 A | 5/1994 | Takahashi et al. |
| 5,334,383 A | 8/1994 | Morrow |
| 5,376,242 A | 12/1994 | Hayakawa |
| 5,388,571 A | 2/1995 | Roberts et al. |
| 5,427,667 A | 6/1995 | Bakhir et al. |
| 5,445,722 A | 8/1995 | Yamaguti et al. |
| 5,474,662 A | 12/1995 | Miyamae |
| 5,507,932 A | 4/1996 | Robinson |
| 5,510,009 A | 4/1996 | Arai et al. |
| 5,543,030 A | 8/1996 | Shiramizu et al. |
| 5,545,374 A | 8/1996 | French et al. |
| 5,560,816 A | 10/1996 | Robinson |
| 5,578,022 A | 11/1996 | Scherson et al. |
| 5,593,554 A | 1/1997 | Yamanaka et al. |
| 5,599,438 A | 2/1997 | Shiramizu et al. |
| 5,615,764 A | 4/1997 | Satoh |
| 5,616,221 A | 4/1997 | Aoki et al. |
| 5,620,587 A | 4/1997 | Nakamura |
| 5,622,725 A | 4/1997 | Kross |
| 5,622,848 A | 4/1997 | Morrow |
| 5,624,535 A | 4/1997 | Tsuchikawa et al. |
| 5,624,544 A | 4/1997 | Deguchi et al. |
| 5,628,888 A | 5/1997 | Bakhir et al. |
| 5,635,040 A | 6/1997 | Bakhir et al. |
| 5,635,053 A | 6/1997 | Aoki et al. |
| 5,662,625 A | 9/1997 | Westwood |
| 5,674,365 A | 10/1997 | Sano |
| 5,674,537 A | 10/1997 | Morrow |
| 5,720,869 A | 2/1998 | Yamanaka et al. |
| 5,728,274 A | 3/1998 | Kamitani et al. |
| 5,728,287 A | 3/1998 | Hough et al. |
| 5,731,008 A | 3/1998 | Morrow |
| 5,736,027 A | 4/1998 | Nakamura |
| 5,759,489 A | 6/1998 | Miura et al. |
| 5,762,779 A | 6/1998 | Shiramizu et al. |
| 5,783,052 A | 7/1998 | Bakhir et al. |
| 5,792,090 A | 8/1998 | Ladin |
| 5,798,028 A | 8/1998 | Tsuchikawa et al. |
| 5,833,831 A | 11/1998 | Kitajima et al. |
| 5,843,291 A | 12/1998 | Eki et al. |
| 5,858,201 A | 1/1999 | Otsuka et al. |
| 5,858,202 A | 1/1999 | Nakamura |
| 5,871,623 A | 2/1999 | Bakhir et al. |
| 5,888,357 A | 3/1999 | Mitsumori et al. |
| 5,897,757 A | 4/1999 | Sano |
| 5,900,257 A | 5/1999 | Breton et al. |
| 5,902,619 A | 5/1999 | Rubow et al. |
| 5,906,810 A | 5/1999 | Turner |
| 5,908,707 A | 6/1999 | Cabell et al. |
| 5,928,488 A | 7/1999 | Newman |
| 5,928,491 A | 7/1999 | Yu et al. |
| 5,932,171 A | 8/1999 | Malchesky |
| 5,938,915 A | 8/1999 | Morisawa |
| 5,938,916 A | 8/1999 | Bryson et al. |
| 5,944,978 A | 8/1999 | Okazaki |
| 5,948,220 A | 9/1999 | Kamitani et al. |
| 5,951,859 A | 9/1999 | Miura et al. |
| 5,963,435 A | 10/1999 | Biernson |
| 5,964,089 A | 10/1999 | Murphy et al. |
| 5,965,009 A | 10/1999 | Shimamune et al. |
| 5,985,110 A | 11/1999 | Bakhir et al. |
| 5,993,639 A | 11/1999 | Miyashita et al. |
| 5,997,717 A | 12/1999 | Miyashita et al. |
| 6,007,686 A | 12/1999 | Welch et al. |
| 6,007,693 A | 12/1999 | Silveri |
| 6,007,696 A | 12/1999 | Takayasu et al. |
| 6,033,539 A | 3/2000 | Gablenko |
| 6,056,866 A | 5/2000 | Maeda et al. |
| 6,059,941 A | 5/2000 | Bryson et al. |
| 6,093,292 A | 7/2000 | Akiyama |
| 6,106,691 A | 8/2000 | Nakamura et al. |
| 6,117,285 A | 9/2000 | Welch et al. |
| 6,121,317 A | 9/2000 | Wu et al. |
| 6,126,796 A | 10/2000 | Shimamune et al. |
| 6,126,810 A | 10/2000 | Fricker et al. |
| 6,139,876 A | 10/2000 | Kolta |
| 6,143,163 A | 11/2000 | Sawamoto et al. |

(56) References Cited

U.S. PATENT DOCUMENTS

| | | | |
|---|---|---|---|
| 6,149,780 A | 11/2000 | Miyake | |
| 6,171,551 B1 | 1/2001 | Malchesky et al. | |
| 6,174,419 B1 | 1/2001 | Akiyama | |
| 6,187,154 B1 | 2/2001 | Yamaguchi et al. | |
| 6,197,814 B1 | 3/2001 | Arata et al. | |
| 6,200,434 B1 | 3/2001 | Shinjo et al. | |
| 6,210,748 B1 | 4/2001 | Nagahara et al. | |
| 6,228,251 B1 | 5/2001 | Okazaki | |
| 6,231,747 B1 | 5/2001 | Fukuzuka et al. | |
| 6,231,878 B1 | 5/2001 | Komatu et al. | |
| 6,251,259 B1 | 6/2001 | Satoh et al. | |
| 6,258,225 B1 | 7/2001 | Yamaoka | |
| 6,277,266 B1 | 8/2001 | Yamaoka | |
| 6,280,594 B1 | 8/2001 | Yamaoka | |
| 6,294,073 B1 | 9/2001 | Shirota et al. | |
| 6,296,744 B1 | 10/2001 | Djeiranishvili et al. | |
| 6,333,054 B1 | 12/2001 | Rogozinski | |
| 6,340,663 B1 | 1/2002 | Deleo et al. | |
| 6,342,150 B1 | 1/2002 | Sale et al. | |
| 6,350,376 B1 | 2/2002 | Imaoka et al. | |
| 6,358,395 B1 | 3/2002 | Schorzman et al. | |
| 6,361,665 B1 | 3/2002 | Voracek | |
| 6,368,592 B1 | 4/2002 | Colton et al. | |
| 6,375,809 B1 | 4/2002 | Kato et al. | |
| 6,384,363 B1 | 5/2002 | Hayakawa et al. | |
| 6,391,169 B1 | 5/2002 | Hara et al. | |
| 6,426,066 B1 | 7/2002 | Najafi et al. | |
| 6,444,255 B2 | 9/2002 | Nagahara et al. | |
| 6,462,250 B1 | 10/2002 | Kuriyama et al. | |
| 6,464,845 B2 | 10/2002 | Shirota et al. | |
| 6,475,371 B1 | 11/2002 | Shirahata et al. | |
| 6,506,416 B1 | 1/2003 | Okauchi et al. | |
| 6,527,940 B1 | 3/2003 | Shimamune et al. | |
| 6,544,502 B2 | 4/2003 | Heesch | |
| 6,551,492 B2 | 4/2003 | Hanaoka | |
| 6,565,736 B2 | 5/2003 | Park et al. | |
| 6,585,867 B1 | 7/2003 | Asano | |
| 6,585,868 B1 | 7/2003 | Chihara | |
| 6,598,602 B1 | 7/2003 | Sjoholm | |
| 6,620,315 B2 | 9/2003 | Martin | |
| 6,623,615 B1 | 9/2003 | Morisawa et al. | |
| 6,623,695 B2 | 9/2003 | Malchesky et al. | |
| 6,624,135 B2 | 9/2003 | Takano | |
| 6,632,347 B1 | 10/2003 | Buckley et al. | |
| 6,638,364 B2 | 10/2003 | Harkins et al. | |
| 6,638,413 B1 | 10/2003 | Weinberg et al. | |
| 6,663,306 B2 | 12/2003 | Policicchio et al. | |
| 6,716,335 B2 | 4/2004 | Takesako et al. | |
| 6,723,226 B1 | 4/2004 | Takayasu et al. | |
| 6,743,351 B1 | 6/2004 | Arai et al. | |
| 6,752,757 B2 | 6/2004 | Muir et al. | |
| 6,815,551 B2 | 11/2004 | Albiez et al. | |
| 6,823,609 B2 | 11/2004 | Moretti | |
| 6,827,849 B2 | 12/2004 | Kurokawa et al. | |
| 6,833,206 B2 | 12/2004 | Erdle et al. | |
| 6,833,207 B2 | 12/2004 | Joos et al. | |
| 6,838,210 B2 | 1/2005 | Sawa | |
| 6,843,448 B2 | 1/2005 | Parmley | |
| 6,844,026 B2 | 1/2005 | Anthony et al. | |
| 6,852,205 B1 | 2/2005 | Toyoshima et al. | |
| 6,855,233 B2 | 2/2005 | Sawada | |
| 6,855,490 B2 | 2/2005 | Sompuram et al. | |
| 6,856,916 B2 | 2/2005 | Shyu | |
| 6,866,756 B2 | 3/2005 | Klein | |
| 6,867,048 B2 | 3/2005 | Kovacs | |
| 6,874,675 B2 | 4/2005 | Kida et al. | |
| 6,887,601 B2 | 5/2005 | Moulthrop et al. | |
| 6,923,893 B2 | 8/2005 | Sano | |
| 7,276,051 B1 | 10/2007 | Henley et al. | |
| 2001/0012544 A1 | 8/2001 | Nagahara et al. | |
| 2001/0022273 A1 | 9/2001 | Popov et al. | |
| 2002/0006961 A1 | 1/2002 | Katz et al. | |
| 2002/0023847 A1 | 2/2002 | Natsume | |
| 2002/0027070 A1 | 3/2002 | Oyokota et al. | |
| 2002/0027079 A1 | 3/2002 | Hanaoka | |
| 2002/0027084 A1 | 3/2002 | Park et al. | |
| 2002/0032141 A1 | 3/2002 | Harkins | |
| 2002/0036134 A1 | 3/2002 | Shirota et al. | |
| 2002/0112314 A1 | 8/2002 | Harkins | |
| 2002/0134691 A1 | 9/2002 | Satoh et al. | |
| 2002/0135220 A1 | 9/2002 | Yamaguchi et al. | |
| 2002/0160053 A1 | 10/2002 | Yahagi et al. | |
| 2002/0165220 A1 | 11/2002 | Heesch | |
| 2002/0165431 A1 | 11/2002 | Muir et al. | |
| 2002/0168418 A1 | 11/2002 | Lorenz et al. | |
| 2002/0175085 A1 | 11/2002 | Harkins et al. | |
| 2002/0176885 A1 | 11/2002 | Najafi et al. | |
| 2002/0179884 A1 | 12/2002 | Hoshino et al. | |
| 2002/0182262 A1 | 12/2002 | Selkon | |
| 2003/0015418 A1 | 1/2003 | Tseng et al. | |
| 2003/0019764 A1 | 1/2003 | Baldwin et al. | |
| 2003/0024828 A1 | 2/2003 | Kondo et al. | |
| 2003/0045502 A1 | 3/2003 | Kataoka et al. | |
| 2003/0049163 A1 | 3/2003 | Malchesky et al. | |
| 2003/0056805 A1 | 3/2003 | Sumita | |
| 2003/0062068 A1 | 4/2003 | Ko et al. | |
| 2003/0064427 A1 | 4/2003 | Felkner et al. | |
| 2003/0087427 A1 | 5/2003 | Colton et al. | |
| 2003/0089618 A1 | 5/2003 | Satoh et al. | |
| 2003/0141200 A1 | 7/2003 | Harada | |
| 2003/0185704 A1 | 10/2003 | Bernard et al. | |
| 2003/0219361 A1 | 11/2003 | Lee et al. | |
| 2003/0230826 A1 | 12/2003 | Kawaguchi et al. | |
| 2004/0004007 A1 | 1/2004 | Orolin et al. | |
| 2004/0011665 A1 | 1/2004 | Koizumi et al. | |
| 2004/0029761 A1 | 2/2004 | Wakamatsu et al. | |
| 2004/0037737 A1 | 2/2004 | Marais et al. | |
| 2004/0055896 A1 | 3/2004 | Anderson et al. | |
| 2004/0060815 A1 | 4/2004 | Buckley et al. | |
| 2004/0079791 A1 | 4/2004 | Kida et al. | |
| 2004/0081705 A1 | 4/2004 | Gotou | |
| 2004/0084325 A1 | 5/2004 | Weinberg et al. | |
| 2004/0084326 A1 | 5/2004 | Weinberg et al. | |
| 2004/0094406 A1 | 5/2004 | Sawada | |
| 2004/0131695 A1 | 7/2004 | Hinze | |
| 2004/0137078 A1 | 7/2004 | Najafi et al. | |
| 2004/0154993 A1 | 8/2004 | Yanagihara et al. | |
| 2004/0168909 A1 | 9/2004 | Larson | |
| 2004/0168933 A1 | 9/2004 | Inoue | |
| 2004/0171701 A1 | 9/2004 | Shaw | |
| 2004/0172985 A1 | 9/2004 | Mamiya et al. | |
| 2004/0177655 A1 | 9/2004 | Kodera et al. | |
| 2004/0185311 A1 | 9/2004 | Muthuswamy et al. | |
| 2004/0185313 A1 | 9/2004 | Halter et al. | |
| 2004/0188248 A1 | 9/2004 | Sawa | |
| 2004/0208940 A1 | 10/2004 | Selkon | |
| 2004/0244537 A1 | 12/2004 | Runyon | |
| 2004/0250323 A1 | 12/2004 | Arai et al. | |
| 2004/0254744 A1 | 12/2004 | Shyu | |
| 2004/0256317 A1 | 12/2004 | Yamada et al. | |
| 2004/0265394 A1 | 12/2004 | Morris et al. | |
| 2005/0000117 A1 | 1/2005 | Polegato Moretti | |
| 2005/0054973 A1 | 3/2005 | Constantz et al. | |
| 2005/0058013 A1 | 3/2005 | Warf et al. | |
| 2005/0062289 A1 | 3/2005 | Cho et al. | |
| 2005/0064259 A1 | 3/2005 | Coors | |
| 2005/0067300 A1 | 3/2005 | Tremblay et al. | |
| 2005/0074421 A1 | 4/2005 | Tanaka | |
| 2005/0075257 A1 | 4/2005 | Scheper et al. | |
| 2005/0101838 A1 | 5/2005 | Camillocci et al. | |
| 2005/0109610 A1 | 5/2005 | Inamoto et al. | |
| 2005/0121334 A1 | 6/2005 | Sumita | |
| 2005/0126927 A1 | 6/2005 | Lindauer et al. | |
| 2005/0126928 A1 | 6/2005 | Hung et al. | |
| 2005/0129996 A1 | 6/2005 | Moulthrop et al. | |
| 2005/0139465 A1 | 6/2005 | Kasuya et al. | |
| 2005/0139808 A1 | 6/2005 | Alimi | |
| 2005/0142157 A1 | 6/2005 | Alimi | |
| 2005/0153858 A1 | 7/2005 | Anthony et al. | |
| 2005/0155863 A1 | 7/2005 | Kovacs et al. | |
| 2005/0161950 A1 | 7/2005 | Borden et al. | |
| 2005/0178349 A1 | 8/2005 | Tse | |
| 2005/0178920 A1 | 8/2005 | Wilson | |
| 2005/0183949 A1 | 8/2005 | Daly et al. | |

(56) References Cited

U.S. PATENT DOCUMENTS

| | | |
|---|---|---|
| 2005/0183964 A1 | 8/2005 | Roberts et al. |
| 2005/0189234 A1 | 9/2005 | Gibson et al. |
| 2005/0189237 A1 | 9/2005 | Sano |
| 2005/0196462 A1 | 9/2005 | Alimi |
| 2005/0198963 A1 | 9/2005 | Wai et al. |
| 2005/0209518 A1 | 9/2005 | Sage et al. |
| 2007/0196434 A1* | 8/2007 | Alimi .................. A61K 33/00 424/434 |

FOREIGN PATENT DOCUMENTS

| | | |
|---|---|---|
| EP | 0 601 891 A1 | 6/1994 |
| EP | 0 636 581 A1 | 7/1994 |
| EP | 0 740 329 A1 | 10/1996 |
| EP | 0 826 636 A1 | 3/1998 |
| EP | 0 841 305 A2 | 5/1998 |
| EP | 0 889 007 A1 | 1/1999 |
| EP | 0 949 205 A1 | 10/1999 |
| EP | 1 038 993 A1 | 9/2000 |
| EP | 1 064 845 A1 | 1/2001 |
| EP | 1 065 265 A1 | 1/2001 |
| EP | 1 074 515 A2 | 2/2001 |
| EP | 1 103 264 A2 | 5/2001 |
| EP | 1 162 176 A1 | 12/2001 |
| EP | 1 314 699 A1 | 5/2003 |
| EP | 1 386 887 A1 | 2/2004 |
| GB | 1 422 795 A | 1/1976 |
| GB | 2253860 A | 9/1992 |
| GB | 2352728 A | 2/2001 |
| JP | 01-194993 A | 8/1989 |
| JP | 01-218682 A | 8/1989 |
| JP | 02-149395 A | 6/1990 |
| JP | 05-228474 A | 9/1993 |
| JP | 05-228475 A | 9/1993 |
| JP | 05-339769 A | 12/1993 |
| JP | 06-182345 A | 7/1994 |
| JP | 06-254567 A | 9/1994 |
| JP | 06-312183 A | 11/1994 |
| JP | 06-335685 A | 12/1994 |
| JP | 07-000966 A | 1/1995 |
| JP | 07-031981 A | 2/1995 |
| JP | 07-075784 A | 3/1995 |
| JP | 07-155760 A | 6/1995 |
| JP | 07-214063 A | 8/1995 |
| JP | 07-323289 A | 12/1995 |
| JP | 07-328640 A | 12/1995 |
| JP | 08-001160 A | 1/1996 |
| JP | 08-052476 A | 2/1996 |
| JP | 08-061788 A | 3/1996 |
| JP | 08-164192 A | 6/1996 |
| JP | 08-326124 A | 12/1996 |
| JP | 09-025236 A | 1/1997 |
| JP | 09-157173 A | 6/1997 |
| JP | 09-290269 A | 11/1997 |
| JP | 10-080686 A | 3/1998 |
| JP | 10-113664 A | 5/1998 |
| JP | 10-128331 A | 5/1998 |
| JP | 10-192860 A | 7/1998 |
| JP | 11-151493 A | 6/1999 |
| JP | 2000-084559 A | 3/2000 |
| JP | 2000-189972 A | 7/2000 |
| JP | 2001-079548 A | 3/2001 |
| JP | 2001-096275 A | 4/2001 |
| JP | 2001-113276 A | 4/2001 |
| JP | 2001-191076 A | 7/2001 |
| JP | 03-236315 B2 | 12/2001 |
| JP | 03-247134 B2 | 1/2002 |
| JP | 2002-145787 A | 5/2002 |
| JP | 03-299250 B2 | 7/2002 |
| JP | 03-338435 B2 | 10/2002 |
| JP | 03-396853 B2 | 4/2003 |
| JP | 2003-236543 A | 8/2003 |
| JP | 03-458341 B2 | 10/2003 |
| JP | 2004-049946 A | 2/2004 |
| JP | 2004-216349 A | 8/2004 |
| JP | 2004-223306 A | 8/2004 |
| JP | 2004-223309 A | 8/2004 |
| JP | 2004-223310 A | 8/2004 |
| JP | 2004-232413 A | 8/2004 |
| JP | 2005-013520 A | 1/2005 |
| JP | 2005-058848 A | 3/2005 |
| SU | 1296156 A1 | 3/1987 |
| WO | WO 95/01137 A1 | 1/1995 |
| WO | WO 96/02271 A1 | 2/1996 |
| WO | WO 96/14835 A1 | 5/1996 |
| WO | WO 96/16555 A1 | 6/1996 |
| WO | WO 97/40814 A1 | 11/1997 |
| WO | WO 97/46489 A1 | 12/1997 |
| WO | WO 97/49638 A | 12/1997 |
| WO | WO 98/03713 A1 | 1/1998 |
| WO | WO 98/17588 A1 | 4/1998 |
| WO | WO 98/27013 A1 | 6/1998 |
| WO | WO 98/42625 A1 | 10/1998 |
| WO | WO 98/58880 A1 | 12/1998 |
| WO | WO 99/00588 A2 | 1/1999 |
| WO | WO 99/28238 A1 | 6/1999 |
| WO | WO 00/33757 A1 | 6/2000 |
| WO | WO 00/76475 A1 | 12/2000 |
| WO | WO 01/13926 A2 | 3/2001 |
| WO | WO 01/54704 A1 | 8/2001 |
| WO | WO 01/56616 A2 | 8/2001 |
| WO | WO 02/04032 A2 | 1/2002 |
| WO | WO 03/000957 A1 | 1/2003 |
| WO | WO 03/024491 A2 | 3/2003 |
| WO | WO 03/042111 A2 | 5/2003 |
| WO | WO 03/048421 A1 | 6/2003 |
| WO | WO 03/076688 A2 | 9/2003 |
| WO | WO 03/103522 A1 | 12/2003 |
| WO | WO 2004/076721 A2 | 9/2004 |
| WO | WO 2004/078654 A2 | 9/2004 |
| WO | WO 2004/079051 A1 | 9/2004 |
| WO | WO 2004/081222 A2 | 9/2004 |
| WO | WO 2004/082690 A1 | 9/2004 |
| WO | WO 2004/092571 A1 | 10/2004 |
| WO | WO 2005/003848 A1 | 1/2005 |
| WO | WO 2005/011417 A2 | 2/2005 |
| WO | WO 2005/020896 A2 | 3/2005 |
| WO | WO 2005/030651 A1 | 4/2005 |
| WO | WO 2005/061394 A1 | 7/2005 |
| WO | WO 2005/065383 A2 | 7/2005 |
| WO | WO 2005/075581 A1 | 8/2005 |
| WO | WO 2005/080639 A1 | 9/2005 |
| WO | WO 2005/082176 A1 | 9/2005 |

OTHER PUBLICATIONS

Allerginc rhinitis and sinusitis [online] retrieved on May 26, 2016 from: http://www.who.int/respiratory/other/Rhinitis_sinusitis/en/#.*

Sinusitis Treatment [online] retrieved on May 26, 2016 from; http://www.everydayhealth.com/sinus-infection/guide/treatments/.*

Arrigo et al., "Cytotoxic effects induced by oxidative stress in culture mammalian cells and protection provided by Hsp27 expression," Methods, 35, 126-138 (2005).

Ayliffe, "Working Party Report: Decontamination of minimally invasive surgical endoscopes and accessories," Journal of Hospital Infection, 45, 263-277 (2000).

Badia et al., "Saline Wound Irrigation Reduces the Postoperative Infection Rate in Guinea Pigs," Journal of Surgical Research, 63, 457-459 (1996).

Bari et al., "Effectiveness of electrolyzed acidic water in killing *Escherichia coli* 0157:H7, *Salmonella enteritidis*, and *Listeria monocytogenes* on the surfaces of tomatoes," J Food Prot., 66(4), 542-548 (2003).

Bari et al., "Chemical and irradiation treatments for killing *Escherichia coli* O157:H7 on alfalfa, radish, and mung bean seeds," J Food Prot., 66(5), 767-774 (2003).

Beckman et al., "The free radical theory of aging matures," Physiol. Rev. 78, 547-581 (1998).

(56) References Cited

OTHER PUBLICATIONS

Boulton, "The Diabetic Foot," in Diabetes: Clinical Management, Chapter 26, 293-306 (1990).
Carlson, "Redox media as a factor in destroying germs," Schriftenreihe des Vereins fuer Wasser-, Boden- and Lufthygiene, 31, 21-39 (1970).
Carton et al., "Hypotonicity induces membrane protrusions and actin remodeling via activation of small GTPases Rac and Cdc42 in Rat-1 fibroblast," Am. J. Physiol. Cell. Physiol., 285, C935-C944 (2003).
Chernomorskii, "Diagram of the electrochemical stability of water", Russian Journal of Physical Chemistry, 51(4), pp. 542-544 (1977) translation of article published in Zhurnal Fizicheskoi Khimii, 51, 924-925 (1977).
Chisholm, "Wound Evaluation and Cleansing," Soft Tissue Emergencies, 10(4), 665-672 (1992).
De Grey, "Reactive oxygen species production in the mitochondrial matrix: implications for the mechanism of mitochondrial mutation accumulation," Rejuvenation Res., 8(1), 13-17 (2005).
Dire et al., "A Comparison of Wound Irrigation Solutions Used in the Emergency Department," Ann Emerg Med., 19(6), 704-708 (1998).
Dressler et al., "Controls, Standards, and Histogram Interpretation in DNA Flow Cytometry," Methods in Cell Biology, 41, Chpt 17, pp. 241-262 (1994).
Dyson et al., "Comparison of the Effects of Moist and Dry Conditions on Dermal Repair," Journal for Investigative Dermatology, 91(5), 434-439 (1988).
Erwin-Toth et al., "Wound Care Selecting the Right Dressing," Am J Nurs., 95(2), 46-51 (1995).
Eventov et al., "Detoxication and Disinfection with Sodium Hypochlorite," Biomedical Engineering, vol. 32, No. 6 (1998).
Fabrizio et al., "Comparison of electrolyzed oxidizing water with various antimicrobial interventions to reduce *Salmonella* species on poultry," Poultry Science, 81(10), pp. 1598-1605 (2002).
Field et al., "Overview of Wound Healing in a Moist Environment," Am J Surg., 167(1A), 2S-6S (1994).
Flint et al., "Virus cultivation, detection and genetics," in Principles of Virology, Molecular Biology, Pathogenesis and Control, Chapter 2, 25-56 (ASM Press 2000).
Fomin et al., "Participation of water [hydroxyl ions] in oxidation-reduction processes," Sostoyanie Rol Vody Biol. Ob'ektakh, Simp., Tiflis, 120-131 (1967) (Abstract only).
Fraga et al., "Ascorbic acid protects against endogenous oxidative DNA damage in human sperm," Proc. Natl. Acad. Sci USA, 88(24), 11003-11006 (1991).
Fraise, "Choosing disinfectants," J Hosp infect, 43, 255-264 (1999).
Frantz, "In Vivo We Trust," Nature Reviews Drug Discovery, No. 2, p. 501 (2003).
Frippiat et al., "Subcytotoxic H2O2 stress triggers a release of transforming growth factor-beta, which induces biomarkers of cellular senescence of human diploie fibroblast, " J. Biol. Chem. 276, 2531-2537 (2001).
Gao et al., "Observation on the effect of disinfection to HBsAg by electrolyzed oxidizing water," Chinese Journal of Epidemiology, 22(1), pp. 40-42 (2001).
Goberdham et al., "A biomarker that identifies senescent human cell in culture and in aging skin in vivo," Proc. Natl. Acad. Sci. USA, 92, 9663-9667 (1995).
Guitierrez et al., "Produccion de agents biologicos par alas terapias genicas y celulares en humanos," Diagnostico molecular en medicina, 265-291 (2003).
Harada, "Behavior of hydrogen peroxide in electrolyzed anode water," Biosci. Biotechnol Biochem., 66(9), 1783-1791 (2002).
Hatto et al., "The physiological property and function of the electrolyzed-ionized calcium Aquamax on water molecular clusters fractionization," Artif. Organs, 21(1), 43-49 (1997). (Abstract only).
Hayashi et al., "Successful treatment of mediastinitis after cardiovascular surgery using electrolyzed strong acid water aqueous solution," Artif Organs, 21, 39-42 (1997).
Higgins et al., "Wound dressings and Topical Agents," The Diabetic Foot, 12(1), 31-40, (1995).
Hinman et al., "Effect of Air Exposure and Occlusion on Experimental Human Skin Wounds," Nature, 200, No. 4904, 377-379 (1963).
Hollander et al., "Laceration Management," Annals of Emergency Medicine, 34(3), 356-367 (1999).
Horiba et al., "Bactericidal effect of electrolyzed neutral water on bacteria isolated from infected root canals," Oral Surg Oral Med Oral Pathol Oral Radio! Endod, 87(1), 83-87 (1999).
Horita et al., "Healing of Fournier's gangrene of the scrotum in a haemodialysis patient after conservative therapy alone," Nephrology Dialysis Transplantation, 15 (3): 419-421 (2000).
Inoue et al., "Trial of electrolyzed strong acid aqueous solution lavage in the treatment of peritonitis and intraperitoneal abscess," Artif Organs, 21(1), 28-31 (1997).
Ivanova et al., "Mechanism of the extracellular antioxidant defend," Experimental Pathology and Parasitology, 4, 49-59 (2000).
Iwasawa et al., "Bactericidal effect of acidic electrolyzed water—comparison of chemical acidic sodium hydrochloride (NaOCl) solution," Kansenshogaku Zasshi—Journal of Japanese Association on Infectious Diseases, 70(9), 915-922 (1996)—Abstract only.
Iwasawa et al., "The influence of pH on bactericidal effects of strong acidic electrolyzed water," Bokin Bobai, 30(10), 635-643, (2002). Abstract.
Jiang et al., "5-Chlorouracil, A Marker of DNA Damage from Hypochlorous Acid during Inflammation," Journal of Biological Chemistry, vol. 278, No. 35, pp. 32834-32840 (2003).
Jeter et al., "Wound Dressings of the Nineties: Indications and Contraindications," Wound Healing, 8(4), 799-816 (1991).
Kaufman et al., "Preventing Diabetic Foot Ulcers," Derm. Nurs., 6(5), 313-320 (1994).
Kim et al., "Roles of oxidation-reduction potential in electrolyzed oxidizing and chemically modified water for the inactivation of food-related pathogens," J Food Prot, 63, 19-24 (2000).
Kim et al., "Efficacy of electrolyzed oxidizing water in inactivating *Salmonella* on alfalfa seeds and sprouts," J Food Prot., 66(2), 208-214 (2003).
Kimbrough et al., "Electrochemical removal of bromide and reduction of THM formation potential in dirnking water," Water Res., 36(19), 4902-4906 (2002).
Kitaoka, K., "On the electrolytic separation factor of tritium," Radioisotopes, 30(5), 247-252 (1981)—Abstract only.
Kiura et al., "Bactericidal activity of electrolyzed acid water from solution containing sodium chloride at low concentration, in comparison with that at high concentration," J Microbiol Methods, 49(3), 285-93 (2002).
Koseki et al., "Decontamination of lettuce using acidic electrolyzed water," J Food Prot., 64(5), 652-658 (2001).
Koseki et al., "Prediction of microbial growth in fresh-cut vegetables treated with acidic electrolyzed water during storage under various temperature conditions," J Food Prot., 64(12), 1935-1942 (2001).
Koseki et al., "Effect of nitrogen gas packaging on the quality and microbial growth of fresh-cut vegetables under low temperatures," J Food Prot., 65(2), 326-332 (2002).
Koseki et al., "Decontaminative effect of frozen acidic electrolyzed water on lettuce," J Food Prot., 65(2), 411-414 (2002).
Koseki et al., "Effect of mild heat pre-treatment with alkaline electrolyzed water on the efficacy of acidic electrolyzed water against *Escherichia coli* O157:H7 and *Salmonella* on lettuce," Food Microbiology, 21(5), 559-566 (2004).
Laing, P., "Diabetic Foot Ulcers," Am J Surg, 167, 31S-36S (1994).
Len et al., "Ultraviolet spectrophotometric characterization and bactericidal properties of electrolyzed oxidizing water as influenced by amperage and pH," J Food Prot, 63, 1534-1537 (2000).
Len et al., "Effects of storage conditions and pH on chlorine loss in electrolyzed oxidizing (EO) water," J Agric Food Chem, 50, 209-212 (2002).
Li et al., "Preliminary study of microbiocide effect and its mechanism of electrolyzed oxidizing water," Chinese Journal of Epidemiology, 17(2), 95-98 (1996).

(56) References Cited

OTHER PUBLICATIONS

Loshon et al., "Analysis of the killing of spores of Bacillus subtilis by a new disinfectant, Sterilox," Journal of Applied Microbiology, 91, 1051-1058 (2001).
Madden et al., "Application of Principles of Fluid Dynamics to Surgical Wound Irrigation," Current Topics in Surgical Research, 3: 85-93 (1971).
Mak et al., "Reactive Oxidant Species in Asthma," Curr Opin Pulm Med, vol. 12, pp. 7-11 (2006).
Mangram et al., "Guideline for prevention of surgical site infection," Infection Control and Hospital Epidemiology, 20 (4): 247-278 (1999).
Marnett, L.J., "Oxyradicals and DNA damage," Carcinogenesis, 21(3), 361-370 (2000).
Martinez, F., "Sterilant for Human Wounds is Changing Patients' Lives" Infection Control Today, 3 pgs. (Nov. 2004), downloaded from http://www.infectioncontroltoday.com/articles/2004/11/sterilant-for-human-wounds-is-changing-patients-l.aspx.
MedlinePlus: AIDS [online] retrieved from http://www.nlm.nih.gov/medlineplus/ency/article/000594.htm on Jan. 16, 2010. May 30, 2009, pp. 1-6.
MedlinePlus: Asthma [online] retrieved from http://www.nlm.nih.gov/medlineplus/ency/article/000141.htm on Jan. 16, 2010. May 21, 2009, pp. 1-5.
MedlinePlus: Multiple Sclerosis [online] retrieved from http://www.nlm.nih.gov/medlineplus/ency/article/000737.htm on Jun. 11, 2009. Jan. 21, 2009, pp. 1-5.
MedlinePlus: Myocarditis [online] retrieved from http://www.nlm.nih.gov/medlineplus/ency/article/000149.htm on Jan. 16, 2010. May 15, 2008, pp. 1-4.
Michida et al., "Biomimetic oxidation of diphenyl sulfide with electrochemical P-450 model system in CH2Cl2 treated with alkaline solution," Yakugaku Zasshi—Journal of the Pharmaceutical Society of Japan, 119(10), 780-785 (1999).
Middleton et al., "Comparison of a solution of super-oxidized water (Sterilox) with glutaraldehyde for the disinfection of bronchoscopes, contaminated in vitro with *Mycobacterium tuberculosis* and *Mycobacterium avium*—intracellulare in sputum," Journal of Hospital Infection, 45, 278-282 (2000).
Miranda-Altamirano et al., "Treatment of 2nd and 3rd Degree Burns in 48 Pediatric Patients Without Routine Antibiotics Routine Using New Super-oxidized Water Technology" Abstract for Meeting of the Texas Surgical Society, San Antonio, TX, Apr. 1-3, 2005 (2 pgs).
Miyamoto et al., "Effectiveness of acidic oxidative potential water in preventing bacterial infection in islet transplantation," Cell Transplantation, 8, 405-411 (1999).
Model, et al., "Effectiveness of electrolyzed oxidized water irrigation in a burn-wound infection," J Trauma Injury, Infection, and Critical Care, 49, 511-514 (2000).
Morita et al., "Disinfection potential of electrolyzed solution containing sodium chloride at low concentrations," J Virol Methods, 85, 163-174 (2000).
Moscati et al., "Comparison of Normal Saline with Tap Water for Wound Irrigation," American Journal of Emergency Medicine, 16(4), 379-385 (1998).
Moyer et al., "Modulation of human fibroblast Gap junction intercellular communication by Hyaluronan," J. Cell. Biol. 196, 165-170 (2003).
Naderi et al., "Oxidative stress-induced apoptosis in dividing fibroblast involves activation of p38 Map kinase and over expression of Bax: Resistance of quiescent cells to oxidative stress," Apoptosis, 8(1), 91-100 (2003).
Nagamatsu et al., "Application of electrolyzed acid water to sterilization of denture base part 1. Examination of sterilization effects on resin plate," Dent. Mater J, 20(2), 148-55, (2001)—Abstract only.
Nagamatsu et al., "Durability of bactericidal activity in electrolyzed neutral water by storage," Dental Materials Journal, 21(2), 93-104 (2002).

Nakae et al., "Effectiveness of electrolyzed oxidized water irrigation in a burn-wound infection model," J Trauma, 49(3): 511-514 (2000).
Nakagawa et al., "Effect of rinsing hydrocolloid impressions using acidic electrolyzed water on surface roughness and surface hardness of stone models," J Oral Sci., 44(3-4), 141-146 (2002)—Abstract only.
Nakagawara et al., "Spectroscopic characterization and the pH dependence of bactericidal activity of the aqueous chlorine solution," Analytical Sciences, 14(4), 691-698 (1998).
Nelson, D., "Newer technologies for endoscope disinfection: electrolyzed acid water and disposable-component endoscope systems," Gasatrointestinal Endoscopy Clinics of North America, (Kerry Holland, Ed.) WB Saunders Co., Philadelphia, PA, vol. 10, No. 2, pp. 319-328 (2000).
O'Neill, "Physiological significance of volume-regulatory transporters," Am. J. Physiol., 276, C995-C1001 (1999).
Ogino et al., "Treatment for abdominal aortic graft infection: irrigation with electrolyzed strong aqueous acid, in-situ grafting, and omentoplasty," Thorac Cardiovasc Surg, 48(1), 43-44 (2000).
Ohno et al., "Mediastinal Irrigation with Superoxidized Water After Open-Heart Surgery: The Safety and Pitfalls of Cardiovascular Surgical Application," Surgery Today, 30, 1055-1056 (2000).
Okubo et al., "Cytotoxicity and microbicidal activity of electrolyzed strong acid water and acidic hypochlorite solution under isotonic conditions," Kansenshogaku Zasshi: Journal of the Japanese Association for Infectious Diseases, 73(10), 1025-1031 (1999)—Abstract only.
Oomori et al., "The efficiency of disinfection of acidic electrolyzed water in the presence of organic materials," Analytical Science, 16, 365-369 (2000).
Otteneder et al., "Correlation of DNA adduct levels with tumor incidence: carcinogenic potency of DNA adducts," Mutat. Res., 424, 237-247 (1999).
Park et al., "Effectiveness of electrolyzed water as a sanitizer for treating different surfaces," J Food Prot., 65(8), 1276-1280 (2002).
Park et al., "Antimicrobial effect of electrolyzed water for inactivating Campylobacter jejuni during poultry washing," International Journal of Food Microbiology, 72(1-2), 77-83 (2002).
Park et al., "Effects of chlorine and pH on efficacy of electrolyzed water for inactivating *Escherichia coli* O157:H7 and *Listeria monocytogenes*," International Journal of Food Microbiology, 91(1), 13-18 (2004).
Piaggesi et al., "Sodium carboxyl-methyl-cellulose dressings in the management of deep ulcerations of diabetic foot," Diabet Med., 18(4), 320-324 (2001).
Powis et al., "Redox signaling and the control of cell growth and death," Pharmacol Ther., 68(1), 149-173 (1995).
Rodeheaver et al., "Identification of the Wound Infection-Potentiating Factors in Soil," American Journal of Surgery, 128(1), 8-14, (1974).
Ruddy et al., "Decontamination in Practice: Endoscopic decontamination: an audit and practical review," Journal of Hospital Infection, 50, 261-268 (2002).
Russell, S.M., "The effect of electrolyzed oxidative water applied using electrostatic spraying on pathogenic and indicator bacteria on the surface of eggs," Poult. Sci., 82(1), 158-162 (2003).
Rutala et al., "New Disinfection and Sterilization Methods," Emerging Infectious Diseases, 7(2), 348-353 (2001).
Sakai, S., "Development of ionic electrolyzed water and its utilities. The preparation of ionic electrolyzed water and its application to disinfection," Kurin Tekunoroji, 6 (3): 53-57 (1996)—Abstract only.
Sakashita et al., "Antimicrobial effects and efficacy on habitually hand-washing of strong acidic electrolyzed water—a comparative study of alcoholic antiseptics and soap and tap water", Kansenshogaku Zasshi: The Journal of the Japanese Association on Infectious Diseases, 76, 373-377 (2002).
Sanders, L., "Diabetes Mellitus: Prevention of Amputation," J Am Pod Med Assoc, 84(7), 322-328 (1994).
Sawada et al., "Complete electrolysis using a microflow cell with an oil/water interface," Anal Chem., 74(5), 1177-1181 (2002).

(56) References Cited

OTHER PUBLICATIONS

Schaap et al., "Singlet Molecule Oxygen and Superoxide Dismutase," JACS, vol. 96, No. 12, pp. 4025-4026 (1974).
Sekiya et al., "Treatment of Infectious Skin Defects or Ulcers with Electrolyzed Strong Acid Aqueous Solution," Artificial Organs, 21 (1), 32-38 (1997).
Selkon et al., "Evaluation of the antimicrobial activity of a new super-oxidized water, Sterilox®, for the disinfection of endoscopes," Journal of Hospital Infection, 41, 59-70 (1999).
Severino et al., "Is ?-galactosidase staining a marker of senescence in vitro and in vivo?" Exp. Cell. Res., 257(1), 162-171 (2000).
Sharma et al., "Treatment of *Escherichia coli* O157:H7 inoculated alfalfa seeds and sprouts with electrolyzed oxidizing water," International Journal of Food Microbiology, 86(3), 231-237 (2003).
Shen et al., "Interactions of selenium compounds with other antioxidants in DNA damage and apoptosis in Human normal keratinocytes," Cancer Epidemiology, Biomarkers, & Prevention, 10(4), 385-390 (2001).
Shetty et al., "Evaluation of microbicidal activity of a new disinfectant: Sterilox® 2500 against *Clostridium difficile* spores, *Helicobacter pylori*, cancomycin resistant *Enterococcus* species, *Candida albicans* and several *Mycobacterium* species," Journal of Hospital Infection, 41, 101-105 (1999).
Shimmura et al., "Acidic Electrolyzed Water in the Disinfection of the Ocular Surface," Experimental Eye Research, 70(1), 1-6 (2000).
Shirahata et al., "Electrolyzed-reduced water scavenges active oxygen species and protects DNA from oxidative damage," Biochem. Biophys. Res. Commun., 234(1), 269-274 (1997).
Singer et al., "Evaluation and Management of Traumatic Lacerations," New England Journal of Medicine, vol. 337., No. 16, pp. 1142-1148 (1997).
Smirnov et al., "Electron exchangers and electron- and ion-exchangers and their use in a water treatment system," Khim. Aktiv. Polim. Ikh Primen, 259-262 (1969)—Abstract only.
Solovyeva et al., "Cleaning effectiveness of root canal irrigation with electrochemically activated anolyte and catholyte solutions: a pilot study," International Endodontic Journal, 33, 494-504 (2000).
Soto et al., "Bacterial sulfate production by biodesulfurization of aromatic hydrocarbons, determined by ion chromatography," J Chromatogr a, 824(1), 45-52 (1998).
Stein, G., "SV-40-transformed human fibroblasts: evidence for cellular aging in pre-crises cells," J Cell Physiol, 125, 36-44 (1985).
Stevenson et al., "Cleansing the Traumatic Wound by High Pressure Syringe Irrigation," JACEP, 5(1), 17-21 (1976).
Sumita et al., "Characteristics and use of acidified water from redox water generator," Shokuhin Kogyo, 40(10), 29-36 (1997)—Abstract only.
Suzuki et al., "Novel products generated from 2'-deoxyguanosine by hypochlorous acid or a myeloperoxidase -H2P2-Cl-system: identification of diimino-imidazole and amino-imidazolone nucleosides," Nucleic Acids Res., 30(11), 2555-2564 (2002) Abstract.
Takeshita et al., "Influence of free residual chlorine concentration and pH on bactericidal effects of electrolyzed water," Bokin Bobai, 29(2), 69-72 (2001).
Takeyoshi et al., "Primary eye irritation and 5-day cumulative skin irritation studies of super oxidized water in rabbits," Oyo Yakuri, 48(3), 173-177 (1994)—Abstract only.
Tanaka et al., "Antimicrobial activity of superoxidized water" Journal of Hospital Infection, 34, 43-49 (1996).
Tanaka et al., "Molecular basis of antiapoptotic effect of immunophilin ligands on hydrogen peroxide-induced apoptosis in human glioma cells," Neurochem Res., 29(8), 1529-1536 (2004).
Tanaka et al., "The use of electrolyzed solutions for the cleaning and disinfecting of dialyzers" Artif. Organs, 24(12), 921-928 (2000).
Tateno et al., "MT-4 plaque formation can distinguish cytopathic substypes of the human immunodeficiency virus (HIV)," Virology, 167, 299-301 (1988).
Upright et al., "Evaluation of Mesalt dressings and continuous wet saline dressings in ulcerating metastatic skin lesions," Cancer Nursing, 17(2), 149-155 (1994).
Valko et al., "Role of oxygen radicals in DNA damage and cancer incidence," Mol Cell Biochem, 266, 37-56 (2004).
Van Britsom et al., "A rapid method for the detection of uranium in surface water," Sci. Total Environ., vols. 173/174, pp. 83-89 (1995).
Venkitanarayanan et al., "Efficacy of Electrolyzed Oxidizing Water for Inactivating *Escherichia coli* O157:H7, *Salmonella enteritidis*, and *Listeria monocytogenes*," Applied and Environmental Microbiology, 65 (9), 4276-4279 (1999).
Veves et al., "A randomized, controlled trial of Promogran (a collagen/oxidized regenerated cellulose dressing) vs standard treatment in the management of diabetic foot ulcers," Arch Surg., 137(7), 822-827 (2002).
Winter, "Formation of the Scab and the Rate of Epithelization of Superficial Wounds in the Skin of the Young Domestic Pig," Nature, 193, 293-294 (1962).
Xakellis et al., "Hydrocolloid versus saline-gauze dressings in treating pressure ulcers: a cost-effectiveness analysis," Arch Phys Med Rehabil., 73(5), 463-9 (1992).
Yahagi et al., "Effect of Electrolyzed Water on Wound Healing," Artificial Organs, 24 (12), 984-987 (2000).
Yang et al., "The effect of pH on inactivation of pathogenic bacteria on fresh-cut lettuce by dipping treatment with electrolyzed water," Journal of Food Science, 68(3), 1013-1017 (2003).
Yoshimoto et al., "Virucidal effect of super oxidized water" Kagaku Ryoho no. Ryoiki, 12(7), 1337-1342 (1996)—Abstract only.
Young et al., "Mechanisms of killing of Bacillus subtilis spores by hypochlorite and chlorine dioxide," J Appl Microbiol, 95, 54-67 (2003).
Zhang et al., "Antioxidant superoxide dismutase attenuates increased endothelial permeability induced by platelet activating factor," Soc Gynecol Investig. 10, 5-10 (2003).
Zinkevich et al., "The effect of super-oxidized water on *Escherichia coli*," Journal of Hospital Infection, 46, 153-156 (2000).
"Sodium Hypochlorite," Iryoyaku Nihon Iuakuhin Shu, 2004 Edition, p. 886.
European Patent Office, Partial International Search Report and Invitation to Pay Additional Search Fees for International Application No. PCT/US2004/043961 (Oct. 4, 2005).
European Patent Office, Supplementary European Search Report for European Patent Application No. 02790029 (Aug. 24, 2005).
European Patent Office, European Search Report for European Patent Application No. 1 103 264 (Sep. 24, 2003).
European Patent Office, European Search Report for European Patent Application No. 1 293 481 (Nov. 6, 2003).
U.S. Patent & Trademark Office, International Search Report for International Application No. PCT/US02/38861 (Feb. 24, 2003).
European Patent Office, International Search Report for International Application No. PCT/US2006/011251 (Sep. 14, 2006).
European Patent Office, Written Opinion of the International Searching Authority for International Application No. PCT/US2006/011251 (Sep. 14, 2006).
European Patent Office, International Search Report for International Application No. PCT/US2006/011252 (Nov. 10, 2006).
European Patent Office, Written Opinion of the International Searching Authority for International Application No. PCT/US2006/011252 (Nov. 10, 2006).

\* cited by examiner

METHOD OF PREVENTING OR TREATING SINUSITIS WITH OXIDATIVE REDUCTIVE POTENTIAL WATER SOLUTION

CROSS-REFERENCE TO RELATED PATENT APPLICATIONS

This application is a continuation of co-pending U.S. patent application Ser. No. 10/916,566, filed Aug. 11, 2004, which is a continuation-in-part of U.S. patent application Ser. No. 10/862,092, filed on Jun. 4, 2004, which claims the benefit of U.S. Provisional Patent Application 60/533,583, filed on Dec. 30, 2003, all of which are hereby incorporated by reference in their entireties.

FIELD OF THE INVENTION

This invention pertains to oxidative reductive potential water solutions and methods of using such solutions.

BACKGROUND OF THE INVENTION

Oxidative reductive potential (ORP) water, also known as super-oxidized water (SWO), can be used as a non-toxic disinfectant to eradicate microorganisms, including bacteria, viruses and spores, in variety of settings. For example, ORP water may be applied in the healthcare and medical device fields to disinfect surfaces and medical equipment. Advantageously, ORP water is environmentally safe and, thus, avoids the need for costly disposal procedures. ORP water also has application in wound care, medical device sterilization, food sterilization, hospitals, consumer households and anti-bioterrorism.

Although ORP water is an effective disinfectant, it has an extremely limited shelf-life, usually only a few hours. As a result of this short lifespan, the production of ORP water must take place in close proximity to where ORP water is to be used as a disinfectant. This means that a healthcare facility, such as a hospital, must purchase, house and maintain the equipment necessary to produce ORP water. Additionally, prior manufacturing techniques have not been able to produce sufficient commercial-scale quantities of ORP water to permit its widespread use as a disinfectant at healthcare facilities.

Accordingly, a need exists for an ORP water that is stable over an extended period of time and methods of using such an ORP water. A need also exists for cost-effective methods of preparing commercial-scale quantities of ORP water. The present invention provides such an ORP water and methods of preparing and using such an ORP water. These and other advantages of the invention, as well as additional inventive features, will be apparent from the description of the invention provided herein.

BRIEF SUMMARY OF THE INVENTION

The present invention provides an oxidative reductive potential (ORP) water solution, wherein the solution is stable for at least twenty-four hours, and methods of using such an ORP water solution. In one embodiment, the present invention provides a method of preventing or treating a condition in a patient, which method comprises administering to the patient a therapeutically effective amount of. The condition can include medical conditions such as, e.g., upper respiratory conditions, systemic infections, and the like.

The present invention additionally provides a method of treating impaired or damaged tissue, which method comprises contacting the impaired or damaged tissue with a therapeutically effective amount of an ORP water solution, wherein the solution is stable for at least twenty-four hours. The method includes treating tissue, which has been impaired or damaged by surgery or which has been impaired or damaged by causes that are not necessarily relate to surgery, e.g., burns, cuts, abrasions, scrapes, rashes, ulcers, puncture wounds, infections, and the like.

The present invention further provides a method of disinfecting a surface, which method comprises contacting the surface with an anti-infective amount of an ORP water solution, wherein the solution is stable for at least twenty-four hours. The surface can be biological, inanimate, or a combination of such surfaces can be disinfected in accordance with the present invention. Biological surfaces include, e.g, muscle tissue, bone tissue, organ tissue, mucosal tissue, and combinations thereof, can be disinfected in accordance with the present invention. Inanimate surfaces include, e.g., surgically implantable devices, prosthetic devices, and medical devices.

The ORP water solution of the invention can be contained within a sealed container and is stable for at least twenty-four hours. The ORP water solution of the invention can comprise anode water and cathode water. In one embodiment, the ORP water solution of the invention comprises hydrogen peroxide and one or more chlorine species. An apparatus and processes for producing the ORP water solution of the present invention also are provided.

DETAILED DESCRIPTION OF THE INVENTION

Figure 1:
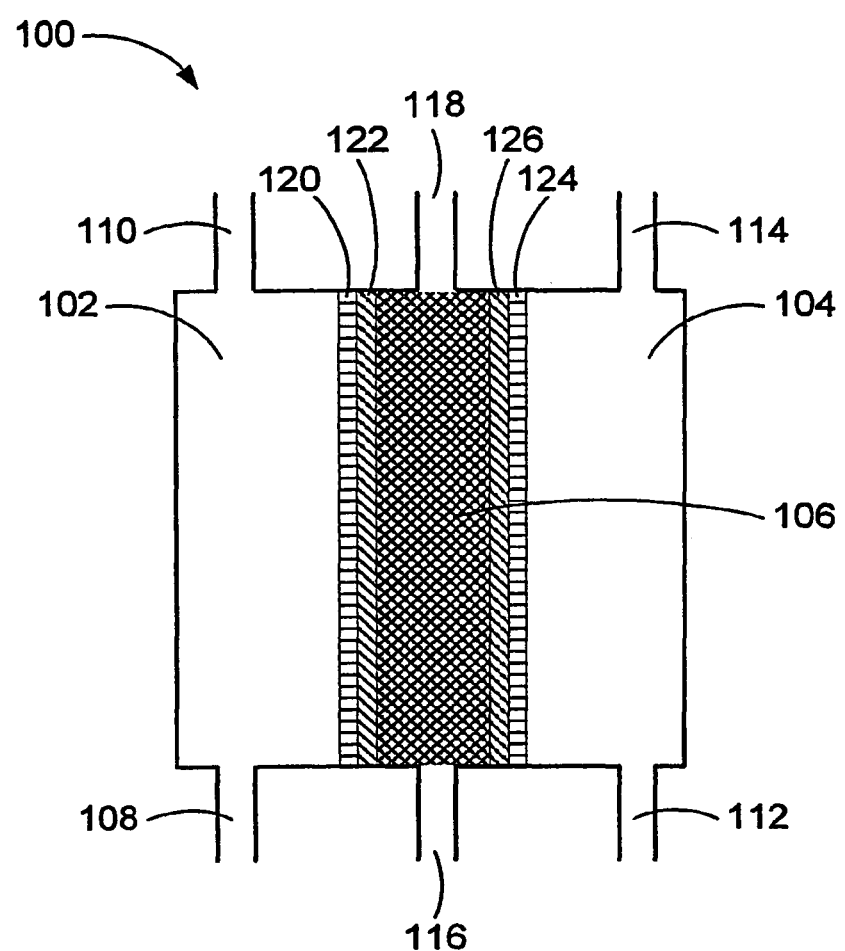
FIG. 1 is a schematic diagram of a three-chambered electrolysis cell for producing an oxidative reductive potential water solution of the present invention.

The present invention provides a method of preventing or treating a condition in a patient, which method comprises administering to the patient a therapeutically effective amount of an oxidative reductive potential (ORP) water solution, wherein the solution is stable for at least twenty-four hours. The condition can include, e.g., medical conditions, illnesses, injuries, allergies, and the like, which are treatable with the ORP water solution of the present invention.

The therapeutically effective amount administered to the patient, e.g., an animal, particularly a human, in the context of the present invention should be sufficient to effect a therapeutic or prophylactic response in the patient over a reasonable time frame. The dose can be readily determined using methods that are well known in the art. One skilled in the art will recognize that the specific dosage level for any particular patient will depend upon a variety of factors. For example, the dose can be determined based on the strength of the particular ORP water solution employed, the severity of the condition, the body weight of the patient, the age of the patient, the physical and mental condition of the patient, general health, sex, diet, and the like. The size of the dose also can be determined based on the existence, nature, and extent of any adverse side effects that might accompany the administration of a particular ORP water solution. It is desirable, whenever possible, to keep adverse side effects to a minimum.

Factors, which can be taken into account for a specific dosage can include, for example, bioavailability, metabolic profile, time of administration, route of administration, rate of excretion, pharmacodynamics associated with a particular ORP water solution in a particular patient, and the like. Other factors can include, e.g., the potency or effectiveness of the ORP water solution with respect to the particular condition to be treated, the severity of the symptoms presented prior to or during the course of therapy, and the like. In some instances, what constitutes a therapeutically effective amount also can be determined, in part, by the use of one or more of the assays, e.g., bioassays, which are reasonably clinically predictive of the efficacy of a particular ORP water solution for the treatment or prevention of a particular condition.

The ORP water solution of the present invention can be administered therapeutically, alone or in combination with one or more other therapeutic agents, to a patient, e.g., a human, e.g., to treat an existing condition. The ORP water solution of the present invention also can be administered prophylactically, alone or in combination with one or more other therapeutic agents, to a patient, e.g., a human, that has been exposed to one or more causative agents associated with the condition. For example, the ORP water solution of the invention can be suitably administered to a patient that has been exposed to one or more infection-causing microorganisms (e.g., viruses, bacteria and/or fungi) prophylactically to inhibit or decrease the likelihood of infection in a patient, or decrease the severity of an infection that develops as a result of such exposure.

One skilled in the art will appreciate that suitable methods of administering the ORP water solution of the present invention are available, and, although more than one route of administration can be used, a particular route can provide a more immediate and more effective reaction than another route. The therapeutically effective amount can be the dose necessary to achieve an "effective level" of the ORP water solution in an individual patient. The therapeutically effective amount can be defined, for example, as the amount required to be administered to an individual patient to achieve a blood level, tissue level, and/or intracellular level of the ORP water of the present invention to prevent or treat the condition in the patient.

When the effective level is used as a preferred endpoint for dosing, the actual dose and schedule can vary depending, for example, upon interindividual differences in pharmacokinetics, distribution, metabolism, and the like. The effective level also can vary when the ORP water solution of the present invention is used in combination with one or more therapeutic agents other than the ORP water solution of the present invention, e.g., one or more anti-infective agents, one or more "moderating," "modulating" or "neutralizing agents," e.g., as described in U.S. Pat. Nos. 5,334,383 and 5,622,848, one or more anti-inflammatory agents, and the like.

An appropriate indicator can be used for determining and/or monitoring the effective level. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as, e.g., the concentration of urinary metabolites, changes in markers associated with the condition (e.g., viral count in the case of a viral infection), decrease in the symptoms associated with the conditions, and the like.

The ORP water of the present invention can be administered using any suitable method of administration known in the art. The ORP water of the present invention can be administered in combination with one or more pharmaceutically acceptable carriers, vehicles, adjuvants, excipients, or diluents, which are known in the art. One skilled in the art can easily determine the appropriate formulation and method of administration for administering the ORP water in accordance with the present invention. Any necessary adjustments in dose can be readily made by a skilled practitioner to address the nature or severity of the condition being treated in view of other factors, such as, e.g., side effects, changes in the patient's overall condition, and the like.

In one embodiment, the condition is an upper respiratory condition, which is treatable by the ORP water solution of the present invention. Any suitable method of administration can be employed for the treatment or prevention of an upper respiratory condition in accordance with the present invention. Preferably, the ORP solution is administered to the upper airway, e.g., so as to contact one or more upper airway tissues associated with the upper respiratory condition. The ORP solution of the present invention can be administered to the upper airway as a steam or a spray. In addition, the ORP water solution of the present invention can be administered by aerosolization, nebulization or atomization. When the ORP water solution of the invention is administered by aerosolization, nebulization or atomization, it is preferably administered in the form of droplets having a diameter in the range of from about 1 micron to about 10 microns.

Methods and devices, which are useful for aerosolization, nebulization and atomization, are well known in the art. Medical nebulizers, for example, have been used to deliver a metered dose of a physiologically active liquid into an inspiration gas stream for inhalation by a recipient. See, e.g., U.S. Pat. No. 6,598,602. Medical nebulizers can operate to generate liquid droplets, which form an aerosol with the inspiration gas. In other circumstances medical nebulizers may be used to inject water droplets into an inspiration gas stream to provide gas with a suitable moisture content to a recipient, which is particularly useful where the inspiration gas stream is provided by a mechanical breathing aid such as a respirator, ventilator or anaesthetic delivery system.

An exemplary nebulizer is described, for example, in WO 95/01137, which describes a hand held device that operates to eject droplets of a medical liquid into a passing air stream (inspiration gas stream), which is generated by a recipient's inhalation through a mouthpiece. Another example can be found in U.S. Pat. No. 5,388,571, which describes a positive-pressure ventilator system which provides control and augmentation of breathing for a patient with respiratory insufficiency and which includes a nebulizer for delivering particles of liquid medication into the airways and alveoli of the lungs of a patient. U.S. Pat. No. 5,312,281 describes an ultrasonic wave nebulizer, which atomizes water or liquid at low temperature and reportedly can adjust the size of mist. In addition, U.S. Pat. No. 5,287,847 describes a pneumatic nebulizing apparatus with scalable flow rates and output volumes for delivering a medicinal aerosol to neonates, children and adults. Further, U.S. Pat. No. 5,063,922 describes an ultrasonic atomizer.

The method of the present invention can be used for preventing or treating an upper respiratory condition, which affects one or more upper respiratory airway tissues, particularly nasal tissue, sinus tissue, and lung tissue. Such upper respiratory conditions can include, for example, a sinusitis (e.g., a rhinosinusitis, an acute sinusitis, a chronic sinusitis, and the like), a pharyngitis, an asthma, and the like, which are preventable or treatable with the ORP solution of the present invention.

Chronic sinusitis typically refers to inflammation of the sinuses that continues for at least 3 weeks, but often continues for months or even years. Allergies are frequently associated with chronic sinusitis. In addition, patients with asthma have a particularly high frequency of chronic sinusitis Inhalation of airborne allergens (substances that provoke an allergic reaction), such as dust, mold, and pollen, often set off allergic reactions (allergic rhinitis) that, in turn, may contribute to sinusitis. People who are allergic to fungi can develop a condition called "allergic fungal sinusitis." Damp weather or pollutants in the air and in buildings also can affect people subject to chronic sinusitis.

Like acute sinusitis, chronic sinusitis is more common in patients with immune deficiency or abnormalities of mucus secretion or movement (e.g., immune deficiency, HIV infection, cystic fibrosis, Kartagener's syndrome). In addition, some patients have severe asthma, nasal polyps, and severe asthmatic responses to aspirin and aspirin-like medications (so-called non-steroidal anti-inflammatory drugs, or NSAIDs). These latter patients have a high frequency of chronic sinusitis.

A doctor can diagnose sinusitis by medical history, physical examination, X-rays, and if necessary, MRIs or CT scans (magnetic resonance imaging and computed tomography). After diagnosing sinusitis and identifying a possible cause, a doctor can prescribe a course of treatment that will reduce the inflammation and relieve the symptoms. Treating acute sinusitis typically requires re-establishing drainage of the nasal passages, controlling or eliminating the source of the inflammation, and relieving the pain. Doctors generally recommend decongestants to reduce the congestion, antibiotics to control a bacterial infection, if present, and pain relievers to reduce the pain.

When treatment with drugs fails, surgery may be the only alternative for treating chronic sinusitis, e.g., removal of adenoids, removal of nasal polyps, repair of a deviated septum, endoscopic sinus surgery, and the like. It is believed that the administration of ORP water in accordance with the method of the present invention can be used for treating chronic sinusitis as an alternative to potentially avoid more aggressive therapies, such as antibiotics and surgery.

With regard to pharyngitis, it is estimated that worldwide, 1 to 2% of all visits to doctors' offices, clinics and emergency rooms are because of pharyngitis. In the United States and Mexico, pharyngitis/tonsillitis accounts for a reported 15 and 12 million consultations per year, respectively. It has been established that these cases are caused by various bacteria and viruses. On the one hand we know that pharyngitis and tonsillitis caused by group A β-hemolytic *Streptococcus* significantly raise the risk of rheumatic fever in poor populations. On the other hand, it is believed that only 5 to 15% of pharyngitis cases are caused by this bacterium, and that the rest of the acute cases are due to bacteria and viruses of little epidemiological relevance. The latter cases tend to be self-limiting in a few days and do not leave sequelae.

It has been verified that a great number of doctors worldwide prescribe antibiotics indiscriminately for acute pharyngitis. This occurs in a daily practice, often because patients tend to request powerful antibiotics. Unfortunately, it is difficult to establish an accurate diagnosis of streptococcal pharyngitis/tonsillitis clinically and the cost/benefit ratio of treating acute pharyngitis/tonsillitis with antibiotics is questionable. In some countries, such as Mexico, the waste of government resources to cover the cost of antibiotics, in addition to working days missed, represent a significant loss with respect to the national budget.

It is believed that the administration of ORP water in accordance with the method of the present invention can be useful for the adjuvant treatment of acute pharyngitis/tonsillitis. The empirical treatment of acute pharyngitis/tonsillitis may begin with administering an ORP water solution in accordance with the present invention, and, depending on evolution or the result of the rapid test for *Streptococcus*, antibiotics may be initiated from 48-72 hours thereafter only if needed. The method of the present invention may thus allow the use of antibiotics to be deferred, and, at the same time, reduce the symptomatology of the patient and accelerate the patient's recovery if the pharyngitis/tonsillitis is not from group A *Streptococcus*. The adjuvant use of an ORP water solution of the present invention with antibiotics for the treatment of streptococcal pharyngitis/tonsillitis also may shorten the period of clinical response and decrease the incidence of recurrences.

The method of the present invention also can be used for the prevention or treatment of an infection, which is treatable with the ORP water solution of the present invention. The infection can be caused by one or more infectious pathogens such as, for example, infectious microorganisms. Such microorganisms can include, for example, viruses, bacteria, and fungi. The viruses can include, e.g., one or more viruses selected from the group consisting of adenoviruses, HIV, rhinoviruses, and flu viruses. The bacteria can include, e.g., one or more bacteria selected from the group consisting of *Escherichia coli, Pseudomonas aeruginosa, Staphylococcus aureus,* and *Mycobaterium tuberculosis*. The fungi can include, e.g., one or more fungi selected from the group consisting of *Candida albicans, Bacillus subtilis* and *Bacillus athrophaeus*. The method of the present invention also can be used for the prevention or treatment of inflammatory conditions or allergic reactions, which are treatable with the ORP water solution of the invention.

In another embodiment, the method of the present invention comprises parenterally administering the ORP water solution of the invention. Parenteral administration can include administering the ORP water solution of the invention intravenously, subcutaneously, intramuscularly, or intraperitoneally. In a preferred embodiment, the ORP water solution of the present invention is administered intravenously to prevent or treat a condition in accordance with the method of the present invention. Suitable conditions can include, e.g., viral myocarditis, multiple sclerosis, and AIDS. See, e.g., U.S. Pat. Nos. 5,334,383 and 5,622,848, which describe methods of treating viral myocarditis, multiple sclerosis, and AIDS via intravenous administration of ORP water solutions.

The present invention additionally provides a method of treating impaired or damaged tissue, which method comprises contacting the impaired or damaged tissue with a therapeutically effective amount of the ORP water solution of the present invention. Any suitable method can be used for contacting the impaired or damaged tissue, so as to treat the impaired or damaged tissue in accordance with the present invention. For example, the impaired or damaged tissue can be treated in accordance with the invention by irrigating the tissue with the ORP water solution of the invention, so as to contact the impaired or damaged tissue with the ORP water. Alternatively (and additionally), the ORP water solution of the present invention can be administered as a steam or a spray, or by aerosolization, nebulization or atomization, as described herein, so as to contact the impaired or damaged tissue with the ORP water.

The method of the present invention can be used in the treatment of tissues, which have been impaired or damaged, e.g., by surgery. For instance, the method of the present invention can be used for treating tissues, which have been impaired or damaged by an incision. In addition, the method of the present invention can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, e.g., root canal surgery, tooth extraction, gum surgery, and the like.

The method of the present invention also includes treating tissues, which have been impaired or damaged by one or more burns, cuts, abrasions, scrapes, rashes, ulcers, puncture wounds, combinations thereof, and the like, which are not necessarily caused by surgery. The method of the present invention also can be used for treating impaired or damaged tissue, which is infected, or tissue impaired or damaged due to infection. Such infection can be caused by one or more infectious pathogens, such as, e.g., one or more microorganisms selected from the group consisting of viruses, bacteria, and fungi, as described herein.

The present invention further provides a method of disinfecting a surface, which method comprises contacting the surface with an anti-infective amount of the ORP water solution of the present invention. In accordance with the method of the present invention, the surface can be contacted using any suitable method. For example, the surface can be contacted by irrigating the surface with the ORP water solution of the invention, so as to disinfect the surface in accordance with the invention. Additionally, the surface can be contacted by applying the ORP water solution of the present invention to the surface as a steam or a spray, or by aerosolization, nebulization or atomization, as described herein, so as to disinfect the surface in accordance with the invention. Further, the ORP water solution of the present invention can be applied to the surface with a cleaning wipe, as described herein. By disinfecting a surface in accordance with the present invention, the surface may be cleansed of infectious microorganisms. Alternatively (or additionally), the ORP water solution of the present invention can be applied to the surface to provide a barrier to infection, thereby disinfecting a surface in accordance with the present invention.

The method of the present invention can be used for disinfecting a surface, which is biological, inanimate, or a combination thereof. Biological surfaces can include, for example, tissues within one or more body cavities such as, for example, the oral cavity, the sinus cavity, the cranial cavity, the abdominal cavity, and the thoracic cavity. Tissues within the oral cavity include, e.g., mouth tissue, gum tissue, tongue tissue, and throat tissue. The biological tissue also can include muscle tissue, bone tissue, organ tissue, mucosal tissue, and combinations thereof. Inanimate surfaces include, for example, surgically implantable devices, prosthetic devices, and medical devices. In accordance with the method of the present invention, the surfaces of internal organs, viscera, muscle, and the like, which may be exposed during surgery, can be disinfected, e.g., to maintain sterility of the surgical environment.

The ORP water of the present invention is produced by an oxidation-reduction process, which can be referred to as an electrolytic or redox reaction, in which electrical energy is used to produce chemical change in an aqueous solution. Electrical energy is introduced into and transported through water by the conduction of electrical charge from one point to another in the form of an electrical current. In order for the electrical current to arise and subsist there must be charge carriers in the water, and there must be a force that makes the carriers move. The charge carriers can be electrons, as in the case of metal and semiconductors, or they can be positive and negative ions in the case of solutions.

A reduction reaction occurs at the cathode while an oxidation reaction occurs at the anode in the process for preparing an ORP water solution according to the invention. The specific reductive and oxidative reactions that occur are described in International Application WO 03/048421 A1.

As used herein, water produced at an anode is referred to as anode water and water produced at a cathode is referred to as cathode water. Anode water contains oxidized species produced from the electrolytic reaction while cathode water contains reduced species from the reaction.

Anode water generally has a low pH typically of from about 1 to about 6.8. Anode water generally contains chlorine in various forms including, for example, chlorine gas, chloride ions, hydrochloric acid and/or hypochlorous acid. Oxygen in various forms is also present including, for example, oxygen gas, peroxides, and/or ozone. Cathode water generally has a high pH typically of from about 7.2 to about 11. Cathode water generally contains hydrogen gas, hydroxyl radicals, and/or sodium ions.

The ORP water solution of the invention may be acidic, neutral or basic, and generally has a pH of from about 1 to about 14. At this pH, the ORP water solution can safely be applied in suitable quantities to hard surfaces without damaging the surfaces or harming objects, such as human skin, that comes into contact with the ORP water solution. Typically, the pH of the ORP water solution is from about 3 to about 8. More preferably, the pH of the ORP water solution is from about 6.4 to about 7.8, and most preferably, the pH is from about 7.4 to about 7.6.

The ORP water solution of the present invention generally has an oxidation-reduction potential of between −1000 millivolts (mV) and +1150 millivolts (mV). This potential is a measure of the tendency (i.e., the potential) of a solution to either accept or transfer electrons that is sensed by a metal electrode and compared with a reference electrode in the same solution. This potential may be measured by standard techniques including, for example, by measuring the electrical potential in millivolts of the ORP water solution relative to standard reference silver/silver chloride electrode. The ORP water generally has a potential between −400 mV and +1300 mV. Preferably, the ORP water solution has a potential between 0 mV and +1250 mV, and more preferably between +500 mV and +1250 mV. Even more preferably, the ORP water of the present invention has a potential of between +800 mV and +1100 mV, and most preferably between +800 mV and +1000 mV.

Various ionic and other species may be present in the ORP water solution of the invention. For example, the ORP water solution may contain chlorine (e.g., free chlorine and bound chlorine), ozone and peroxides (e.g., hydrogen peroxide). The presence of one or more of these species is believed to contribute to the disinfectant ability of the ORP water solution to kill a variety of microorganisms, such as bacteria and fungi, as well as viruses.

Free chlorine typically includes, but is not limited to, hypochlorous acid (HClO), hypochlorite ions (ClO$^-$), sodium hypochlorite (NaOCl), chloride ion (Cl$^-$), chlorite ions (ClO$_2^-$), chlorine dioxide (ClO$_2$), dissolved chlorine gas ($Cl_2$), and other radical chlorine species. The ratio of hypochlorous acid to hypochlorite ion is dependent upon pH. At a pH of 7.4, hypochlorous acid levels are from about 25 ppm to about 75 ppm. Temperature also impacts the ratio of the free chlorine component.

Bound chlorine is chlorine in chemical combination with ammonia or organic amines (e.g., chloramines). Bound chlorine is generally present in an amount up to about 20 ppm.

Chlorine, ozone and hydrogen peroxide may present in the ORP water solution of the invention in any suitable amount. The levels of these components may be measured by methods known in the art.

Typically, the total chlorine content, which includes both free chlorine and bound chlorine, is from about 50 parts per million (ppm) to about 200 ppm. Preferably, the total chlorine content is about 80 ppm to about 150 ppm.

The chlorine content may be measured by methods known in the art, such as the DPD colorimeter method (Lamotte Company, Chestertown, Md.) or other known methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value. The amount of bound chlorine present is then determined by subtracting free chlorine from the total chlorine.

Typically, chlorine dioxide is present in an amount of from about 0.01 ppm to about 5 ppm, preferably from about 1.0 ppm to about 3.0 ppm, and more preferably from about 1.0 ppm to about 1.5 ppm. Chlorine dioxide levels may be measured using a modified DPD colorimeter test. Forms of chlorine other than chlorine dioxide are removed by the addition of the amino acid glycine. Chlorine dioxide reacts directly with the DPD reagent to yield a pink color that is measured by a colorimeter machine.

Ozone is generally present in an amount of from about 0.03 ppm to about 0.2 ppm, and preferably from about 0.10 ppm to about 0.16 ppm. Ozone levels may be measured by known methods, such as by a colorimetric method as described in Bader and Hoigne, *Water Research*, 15, 449-456 (1981).

Hydrogen peroxide levels in the ORP water solution are generally in the range of about 0.01 ppm to about 200 ppm, and preferably between about 0.05 ppm and about 100 ppm. More preferably, hydrogen peroxide is present in an amount between about 0.1 ppm and about 40 ppm, and most preferably between about 1 ppm and 4 ppm. Peroxides (e.g., $H_2O_2$, $H_2O_2^-$ and $HO_2^-$) are generally present in a concentration of less than 0.12 milliMolar (mM).

The level of the hydrogen peroxide can be measured by electron spin resonance (ESR) spectroscopy. Alternatively, it can be measured by a DPD method as described in Bader and Hoigne, *Water Research*, 22, 1109-1115 (1988) or any other suitable method known in the art.

The total amount of oxidizing chemical species present in the ORP water solution is in the range of about 2 millimolar (mM) which includes the aforementioned chlorine species, oxygen species, and additional species that may be difficult to measure such as $Cl^-$, $ClO_3$, $Cl_2^-$, and $ClO_x$. The level of oxidizing chemical species present may also be measured by ESR spectroscopy (using Tempone H as the spin trap molecule).

The ORP water solution of the invention is generally stable for at least twenty-hours, and typically at least two days. More typically, the water solution is stable for at least one week (e.g., one week, two weeks, three weeks, four weeks, etc.), and preferably at least two months. More preferably, the ORP water solution is stable for at least six months after its preparation. Even more preferably, the ORP water solution is stable for at least one year, and most preferably for at least three years.

As used herein, the term stable generally refers to the ability of the ORP water solution remain suitable for its intended use, for example, in decontamination, disinfection, sterilization, anti-microbial cleansing, and wound cleansing, for a specified period of time after its preparation under normal storage conditions (i.e., room temperature).

The ORP water solution of the invention is also stable when stored under accelerated conditions, typically about 30° C. to about 60° C., for at least 90 days, and preferably 180 days.

The concentrations of ionic and other species present solution are generally maintained during the shelf-life of the ORP water solution. Typically, the concentrations of free chlorine, chlorine dioxide, ozone and hydrogen peroxides are maintained at about 70% or great from their initial concentration for at least two months after preparation of the ORP water solution. Preferably, these concentrations are maintained at about 80% or greater of their initial concentration for at least two months after preparation of the ORP water solution. More preferably, these concentrations are at about 90% or greater of their initial concentration for at least two months after preparation of the ORP water solution, and most preferably, about 95% or greater.

The stability of the ORP water solution of the invention may be determined based on the reduction in the amount of organisms present in a sample following exposure to the ORP water solution. The measurement of the reduction of organism concentration may be carried out using any suitable organism including bacteria, fungi, yeasts, or viruses. Suitable organisms include, but are not limited to, *Escherichia coli, Staphylococcus aureus, Candida albicans*, and *Bacillus athrophaeus* (formerly *B. subtilis*). The ORP water solution is useful as both a low-level disinfectant capable of a four log ($10^4$) reduction in the concentration of live microorganisms and a high-level disinfectant capable of a six log ($10^6$) reduction in concentration of live microorganisms.

In one aspect of the invention, the ORP water solution is capable of yielding at least a four log ($10^4$) reduction in total organism concentration following exposure for one minute, when measured at least two months after preparation of the solution. Preferably, the ORP water solution is capable of such a reduction of organism concentration when measured at least six months after preparation of the solution. More preferably, the ORP water solution is capable of such a reduction of organism concentration when measured at least one year after preparation of the ORP water solution, and most preferably when measured at least three years after preparation of the ORP water solution.

In another aspect of the invention, the ORP water solution is capable of at least a six log ($10^6$) reduction in the concentration of a sample of live microorganisms selected from the group consisting of *Escherichia coli, Pseudomonas aeruginosa, Staphylococcus aureus* and *Candida albicans* within one minute of exposure, when measured at least two months after preparation of the ORP water solution. Preferably, the ORP water solution is capable of achieving this reduction of *Escherichia coli, Pseudomonas aeruginosa, Staphylococcus aureus* or *Candida albicans* organisms when measured at least six months after preparation, and more preferably at least one year after preparation. Preferably, the ORP water solution is capable of at least a seven log ($10^7$) reduction in the concentration of such live microorganism within one minute of exposure, when measured at least two months after preparation.

The ORP water solution of the invention is generally capable of reducing a sample of live microorganisms including, but not limited to, *Escherichia coli, Pseudomonas aeruginosa, Staphylococcus aureus* and *Candida albicans*, from an initial concentration of between about $1\times10^6$ and about $1\times10^8$ organisms/ml to a final concentration of about zero organisms/ml within one minute of exposure, when measured at least two months after preparation of the ORP water solution. This is between a six log ($10^6$) and eight log ($10^8$) reduction in organism concentration. Preferably, the ORP water solution is capable of achieving this reduction of *Escherichia coli, Pseudomonas aeruginosa, Staphylococcus aureus* or *Candida albicans* organisms when measured at least six months after preparation, and more preferably at least one year after preparation.

Alternatively, the ORP water solution is capable of a six log ($10^6$) reduction in the concentration of a spore suspension of *Bacillus athrophaeus* spores within about five minutes of exposure, when measured at least two months after preparation of the ORP water solution. Preferably, the ORP water solution is capable of achieving this reduction in the concentration of *Bacillus athrophaeus* spores when measured at least six months after preparation, and more preferably at least one year after preparation.

The ORP water solution is further capable of a four log ($10^4$) reduction in the concentration of a spore suspension of *Bacillus athrophaeus* spores within about thirty (30) seconds of exposure, when measured at least two months after preparation of the ORP water solution. Preferably, the ORP water solution is capable of achieving this reduction in the concentration of *Bacillus athrophaeus* spores when measured at least six months after preparation, and more preferably at least one year after preparation.

The ORP water solution is also capable of a six log ($10^6$) reduction in the concentration of fungal spores, such as *Aspergillis niger* spores, within about five to about ten minutes of exposure, when measured at least two months after preparation of the ORP water solution. Preferably, the ORP water solution is capable of achieving this reduction in the concentration of fungal spores when measured at least six months after preparation, and more preferably at least one year after preparation.

In one embodiment, the ORP water solution of the invention comprises hydrogen peroxide ($H_2O_2$) and one or more chlorine species. Preferably, the chlorine species present is a free chlorine species. The free chlorine species may be selected from the group consisting of hypochlorous acid (HOCl), hypochlorite ions ($OCl^-$), sodium hypochlorite (NaOCl), chlorite ions ($ClO_2^-$), chloride ion ($Cl^-$), chlorine dioxide ($ClO_2$), dissolved chlorine gas ($Cl_2$), and mixtures thereof.

Hydrogen peroxide is present in the ORP water solution generally in the range of about 0.01 ppm to about 200 ppm, and preferably between about 0.05 ppm and about 100 ppm. More preferably, hydrogen peroxide is present in an amount between about 0.1 ppm and about 40 ppm, and most preferably between about 1 ppm and 4 ppm.

The total amount of free chlorine species is generally between about 10 ppm and about 400 ppm, preferably between about 50 ppm and about 200 ppm, and most preferably between about 50 ppm and about 80 ppm. The amount of hypochlorous acid is in the generally between about 15 ppm and about 35 ppm. The amount of sodium hypochlorite is generally in the range of about 25 ppm and about 50 ppm. Chlorine dioxide levels are generally less than about 5 ppm.

The ORP water solution comprising hydrogen peroxide and one or more chlorine species is stable as described herein. Generally, the ORP water solution is stable for at least one week. Preferably, the ORP water solution is stable for at least two months, more preferably, the ORP water solution is stable for at least six months after its preparation. Even more preferably, the ORP water solution is stable for at least one year, and most preferably for at least three years.

The pH of the ORP water solution in this embodiment is generally between about 6 to about 8. Preferably, the pH of the ORP water solution is between about 6.2 and about 7.8, and most preferably between about 7.4 and about 7.6. An exemplary ORP water solution of the present invention can comprise, e.g., from about 1 ppm to about 4 ppm hydrogen peroxide, from about 15 ppm to about 35 ppm hypochlorous acid, from about 25 ppm to about 50 ppm sodium hypochlorite, a pH of from about 6.2 to about 7.8, and is stable for at least one week.

While in no way limiting the present invention, it is believed that the control of pH permits a stable ORP water solution in which hydrogen peroxide and chlorine species, such as, by way of example, hypochlorous acid and hypochlorite ions, coexist.

Following its preparation, the ORP water solution of the invention may be transferred to a sealed container for distribution and sale to end users such as, for example, health care facilities including hospitals, nursing homes, doctor offices, outpatient surgical centers, dental offices, and the like. Any suitable sealed container may be used that maintains the sterility and stability of the ORP water solution held by the container. The container may be constructed of any material that is compatible with the ORP water solution. The container should be generally non-reactive so that the ions present in the ORP water solution do not react with the container to any appreciable extent.

Preferably, the container is constructed of plastic or glass. The plastic may be rigid so that the container is capable of being stored on a shelf. Alternatively, plastic may be flexible, such as a flexible bag.

Suitable plastics include polypropylene, polyester terephthalate (PET), polyolefin, cycloolefin, polycarbonate, ABS resin, polyethylene, polyvinyl chloride, and mixtures thereof. Preferably, the container comprises polyethylene selected from the group consisting of high-density polyethylene (HDPE), low-density polyethylene (LDPE), and linear low-density polyethylene (LLDPE). Most preferably, the container is high density polyethylene.

The container has an opening to permit dispensing of the ORP water solution. The container opening may be sealed in any suitable manner. For example, the container may be sealed with a twist-off cap or stopper. Optionally, the opening may be further sealed with a foil layer.

The headspace gas of the sealed container may be air or other suitable gas that does not react with the ORP water solution. Suitable headspace gases included nitrogen, oxygen, and mixtures thereof.

The invention further provides an ORP water solution comprising anode water and cathode water. Anode water is produced in the anode chamber of the electrolysis cell used in the present invention. Cathode water is produced in the cathode chamber of the electrolysis cell.

Cathode water is generally present in the ORP water solution of the solution in an amount of from about 10% by volume to about 90% by volume of the solution. Preferably, cathode water is present in the ORP water solution in an amount of from about 10% by volume to about 50% by volume, more preferably of from about 20% by volume to about 40% by volume of the solution, and most preferably of from about 20% by volume to about 30% by volume of the solution. Additionally, anode water may be present in the ORP water solution in an amount of from about 50% by volume to about 90% by volume of the solution.

As noted herein, the ORP water solution containing both anode water and cathode water can be acidic, neutral or basic, and generally has a pH of from about 1 to about 14. Typically, the pH of the ORP water solution is from about 3 to about 8. Preferably, the pH is about 6.4 to about 7.8, and more preferably from about 7.4 to about 7.6.

The ORP water solution of the invention has a wide variety of uses as a disinfectant, cleanser, cleaner, antiseptic and the like to control the activity of unwanted or harmful substances present in the environment. Substances that may be treated with the ORP water solution include, for example, organisms and allergens.

The ORP water solution may be used as a disinfectant, sterilization agent, decontaminant, antiseptic and/or cleanser. The ORP water solution of the invention is suitable for use in the following representative applications: medical, dental and/or veterinary equipment and devices; food industry (e.g., hard surfaces, fruits, vegetables, meats); hospitals/health care facilities (e.g., hard surfaces); cosmetic industry (e.g., skin cleaner); households (e.g., floors, counters, hard surfaces); electronics industry (e.g., cleaning circuitry, hard drives); and bio-terrorism (e.g., anthrax, infectious microbes).

The ORP water solution may also be applied to humans and/or animals to treat various conditions including, for example, the following: surgical/open wound cleansing agent; skin pathogen disinfection (e.g., for bacteria, mycoplasmas, virus, fungi, prions); battle wound disinfection; wound healing promotion; burn healing promotion; treatment of stomach ulcers; wound irrigation; skin fungi; psoriasis; athlete's foot; pinkeye and other eye infections; ear infections (e.g., swimmer's ear); lung/nasal/sinus infections; and other medical applications on or in the human or animal body. The use of ORP water solutions as a tissue cell growth promoter is further described in U.S. Patent Application Publication 2002/0160053 A1.

While in no way limiting the present invention, it is believed that the ORP water solution eradicates the bacteria with which it contacts as well as destroying the bacterial cellular components including proteins and DNA.

Organisms that can be controlled, reduced, killed or eradicated by treatment with the ORP water solution include, but are not limited to, bacteria, fungi, yeasts, and viruses. Susceptible bacteria include, but are not limited to, *Escherichia coli, Staphylococcus aureus, Bacillus athrophaeus, Streptococcus pyogenes, Salmonella choleraesuis, Pseudomonas aeruginosa, Shingella dysenteriae*, and other susceptible bacteria. Fungi and yeasts that may be treated with the ORP water solution include, for example, *Candida albicans* and *Trichophyton mentagrophytes*. The ORP water solution may also be applied to viruses including, for example, adenovirus, human immunodeficiency virus (HIV), rhinovirus, influenza (e.g., influenza A), hepatitis (e.g., hepatitis A), coronavirus (responsible for Severe Acute Respiratory Syndrome (SARS)), rotavirus, respiratory syncytial virus, herpes simplex virus, varicella zoster virus, rubella virus, and other susceptible viruses.

The ORP water of the invention is also suitable for use in controlling the activity of allergens present in the environment. As used herein, allergens include any substance other than bacteria, fungi, yeasts, or viruses, that can trigger an adverse immune response, or allergy, in susceptible people or animals. Asthma is a common physiological response following exposure to one or more allergens. Allergens may be either viable (i.e., from living or dead organisms) or non-viable (e.g., non-living such as textiles), and may be present in the environment, for example, in households and/or workplaces.

Protein-based household allergens that may be treated with the ORP water include, for example, animal fur, skin, and feces, household dust, weeds, grasses, trees, mites, and pollens. Animal allergens include, for example, cat epithelium, dog epithelium, horse dander, cow dander, dog dander, guinea pig epithelium, goose feathers, mouse epithelium, mouse urine, rat epithelium and rat urine.

Occupational allergens include, for example, high-molecular-weight agents, such as natural proteins generally derived from plant or animal proteins, and low-molecular-weight chemicals, such as diisocyanates, and other material found in some textiles. Other chemical allergens that may be present in the workplace include, for example, anhydrides, antibiotics, wood dust and dyes. Numerous proteins may be occupational allergens including vegetable gums, enzymes, animal proteins, insects, plant proteins, and legumes.

Additional allergens suitable for treatment by the ORP water solution are described in Korenblat and Wedner, Allergy Theory and Practice (1992) and Middleton, Jr., Allergy Principles and Practice (1993).

The ORP water solution of the invention may be used or applied in any suitable amount to provide the desired bactericidal, virucidal, germicidal and/or anti-allergenic effect.

The ORP water solution may be applied to disinfect and sterilize in any suitable manner. For example, to disinfect and sterilize medical or dental equipment, the equipment is maintained in contact with the ORP water solution for a sufficient period of time to reduce the level of organisms present on the equipment to a desired level.

For disinfection and sterilization of hard surfaces, the ORP water solution may be applied to the hard surface directly from a container in which the ORP water solution is stored. For example, the ORP water solution may be poured, sprayed or otherwise directly applied to the hard surface. The ORP water solution may then be distributed over the hard surface using a suitable substrate such as, for example, cloth, fabric or paper towel. In hospital applications, the substrate is preferably sterile. Alternatively, the ORP water solution may first be applied to a substrate such as cloth, fabric or paper towel. The wetted substrate is then contacted with the hard surface. Alternatively, the ORP water solution may be applied to hard surfaces by dispersing the solution into the air as described herein. The ORP water solution may be applied in a similar manner to humans and animals.

An implement may optionally be used to apply the ORP water solution to hard surfaces such as floors, walls, and ceilings. For example, the ORP water solution may be dispensed onto a mop head for application to floors. Other suitable implements for applying the ORP water solution to hard surfaces are described in U.S. Pat. No. 6,663,306.

The invention further provides a cleaning wipe comprising a water insoluble substrate and the ORP water solution as described herein, wherein the ORP water solution is dispensed onto the substrate. The ORP water solution may be impregnated, coated, covered or otherwise applied to the substrate. Preferably, the substrate is pretreated with the ORP water solution before distribution of the cleaning wipes to end users.

The substrate for the cleaning wipe may be any suitable water-insoluble absorbent or adsorbent material. A wide variety of materials can be used as the substrate. It should have sufficient wet strength, abrasivity, loft and porosity. Further, the substrate must not adversely impact the stability of the ORP water solution. Examples include non woven substrates, woven substrates, hydroentangled substrates and sponges.

The substrate may have one or more layers. Each layer may have the same or different textures and abrasiveness. Differing textures can result from the use of different combinations of materials or from the use of different manufacturing processes or a combination thereof. The substrate should not dissolve or break apart in water. The substrate provides the vehicle for delivering the ORP water solution to the surface to be treated.

The substrate may be a single nonwoven sheet or multiple nonwoven sheets. The nonwoven sheet may be made of wood pulp, synthetic fibers, natural fibers, and blends thereof. Suitable synthetic fibers for use in the substrate include, without limitation, polyester, rayon, nylon, polypropylene, polyethylene, other cellulose polymers, and mixtures of such fibers. The nonwovens may include nonwoven fibrous sheet materials which include meltblown, coform, air-laid, spun bond, wet laid, bonded-carded web materials, hydroentangled (also known as spunlaced) materials, and combinations thereof. These materials can comprise synthetic or natural fibers or combinations thereof. A binder may optionally be present in the substrate.

Examples of suitable nonwoven, water insoluble substrates include 100% cellulose Wadding Grade 1804 from Little Rapids Corporation, 100% polypropylene needlepunch material NB 701-2.8-W/R from American Nonwovens Corporation, a blend of cellulosic and synthetic fibres-Hydraspun 8579 from Ahlstrom Fibre Composites, and 70% Viscose/30% PES Code 9881 from PGI Nonwovens Polymer Corp. Additional examples of nonwoven substrates suitable for use in the cleaning wipes are described in U.S. Pat. Nos. 4,781,974, 4,615,937, 4,666,621, and 5,908,707, and International Patent Application Publications WO 98/03713, WO 97/40814, and WO 96/14835.

The substrate may also be made of woven materials, such as cotton fibers, cotton/nylon blends, or other textiles. Regenerated cellulose, polyurethane foams, and the like, which are used in making sponges, may also be suitable for use.

The liquid loading capacity of the substrate should be at least about 50%-1000% of the dry weight thereof, most preferably at least about 200%-800%. This is expressed as loading ½ to 10 times the weight of the substrate. The weight of the substrate varies without limitation from about 0.01 to about 1,000 grams per square meter, most preferably 25 to 120 grams/m$^2$ (referred to as "basis weight") and typically is produced as a sheet or web which is cut, die-cut, or otherwise sized into the appropriate shape and size. The cleaning wipes will preferably have a certain wet tensile strength which is without limitation about 25 to about 250 Newtons/m, more preferably about 75-170 Newtons/m.

The ORP water solution may be dispensed, impregnated, coated, covered or otherwise applied to the substrate by any suitable method. For example, individual portions of substrate may be treated with a discrete amount of the ORP water solution. Preferably, a mass treatment of a continuous web of substrate material with the ORP water solution is carried out. The entire web of substrate material may be soaked in the ORP water solution. Alternatively, as the substrate web is spooled, or even during creation of a nonwoven substrate, the ORP water solution is sprayed or metered onto the web. A stack of individually cut and sized portions of substrate may be impregnated or coated with the ORP water solution in its container by the manufacturer.

The cleaning wipes may optionally contain additional components to improve the properties of the wipes. For example, the cleaning wipes may further comprise polymers, surfactants, polysaccharides, polycarboxylates, polyvinyl alcohols, solvents, chelating agents, buffers, thickeners, dyes, colorants, fragrances, and mixtures thereof to improve the properties of the wipes. These optional components should not adversely impact the stability of the ORP water solution. Examples of various components that may optionally be included in the cleaning wipes are described in U.S. Pat. Nos. 6,340,663, 6,649,584 and 6,624,135.

The cleaning wipes of the invention can be individually sealed with a heat-sealable or glueable thermoplastic overwrap (such as polyethylene, Mylar, and the like). The wipes can also be packaged as numerous, individual sheets for more economical dispensing. The cleaning wipes may be prepared by first placing multiple sheets of the substrate in a dispenser and then contacting the substrate sheets with the ORP water solution of the invention. Alternatively, the cleaning wipes can be formed as a continuous web by applying the ORP water solution to the substrate during the manufacturing process and then loading the wetted substrate into a dispenser.

The dispenser includes, but is not limited to, a canister with a closure, or a tub with closure. The closure on the dispenser is to seal the moist wipes from the external environment and to prevent premature volatilization of the liquid ingredients.

The dispenser may be made of any suitable material that is compatible with both the substrate and the ORP water solution. For example, the dispenser may be made of plastic, such as high density polyethylene, polypropylene, polycarbonate, polyethylene terephthalate (PET), polyvinyl chloride (PVC), or other rigid plastics.

The continuous web of wipes may be threaded through a thin opening in the top of the dispenser, most preferably, through the closure. A means of sizing the desired length or size of the wipe from the web would then be needed. A knife blade, serrated edge, or other means of cutting the web to desired size may be provided on the top of the dispenser, for non-limiting example, with the thin opening actually doubling in duty as a cutting edge. Alternatively, the continuous web of wipes may be scored, folded, segmented, perforated or partially cut into uniform or non-uniform sizes or lengths, which would then obviate the need for a sharp cutting edge. Further, the wipes may be interleaved, so that the removal of one wipe advances the next.

The ORP water solution of the invention may alternatively be dispersed into the environment through a gaseous medium, such as air. The ORP water solution may be dispersed into the air by any suitable means. For example, the ORP water solution may be formed into droplets of any suitable size and dispersed into a room.

For small scale applications, the ORP water solution may be dispensed through a spray bottle that includes a standpipe and pump. Alternatively, the ORP water solution may be packaged in aerosol containers. Aerosol containers generally include the product to be dispensed, propellant, container, and valve. The valve includes both an actuator and dip tube. The contents of the container are dispensed by pressing down on the actuator. The various components of the aerosol container are compatible with the ORP water solution. Suitable propellants may include a liquefied halocarbon, hydrocarbon, or halocarbon-hydrocarbon blend, or a compressed gas such as carbon dioxide, nitrogen, or nitrous oxide. Aerosol systems typically yield droplets that range in size from about 0.15 μm to about 5 μm.

The ORP water solution may be dispensed in aerosol form as part of an inhaler system for treatment of infections in the lungs and/or air passages or for the healing of wounds in such parts of the body.

For larger scale applications, any suitable device may be used to disperse the ORP water solution into the air including, but not limited to, humidifiers, misters, foggers, vaporizers, atomizers, water sprays, and other spray devices. Such devices permit the dispensing of the ORP water solution on a continuous basis. An ejector which directly mixes air and water in a nozzle may be employed. The ORP water solution may be converted to steam, such as low pressure steam, and released into the air stream. Various types of humidifiers may be used such as ultrasonic humidifiers, stream humidifiers or vaporizers, and evaporative humidifiers.

The particular device used to disperse the ORP water solution may be incorporated into a ventilation system to provide for widespread application of the ORP water solution throughout an entire house or healthcare facility (e.g., hospital, nursing home, etc.).

The ORP water solution may optionally contain a bleaching agent. The bleaching agent may be any suitable material that lightens or whitens a substrate. The ORP water solution containing a bleaching agent can be used in home laundering to disinfect and sterilize bacteria and germs as well as brighten clothing. Suitable bleaching agents include, but are not limited to, chlorine-containing bleaching agents and peroxide-containing bleaching agents. Mixtures of bleaching agents may also be added to the ORP water solution. Preferably, the bleaching agent is added in the form of an aqueous solution to the ORP water solution.

Chlorine-containing bleaching agents useful in the present invention include chlorine, hypochlorites, N-chloro compounds, and chlorine dioxide. Preferably, the chlorine-containing bleaching agent added to the ORP water solution is sodium hypochlorite or hypochlorous acid. Other suitable chlorine-containing bleaching agents include chlorine, calcium hypochlorite, bleach liquor (e.g., aqueous solution of calcium hypochlorite and calcium chloride), bleaching powder (e.g., mixture of calcium hypochlorite, calcium hydroxide, calcium chloride, and hydrates thereof), dibasic magnesium hypochlorite, lithium hypochlorite, chlorinated trisodium phosphate. Mixtures of chlorine-containing bleaching agents may be used.

The addition of a bleaching agent to the ORP water solution may be carried out in any suitable manner. Preferably, an aqueous solution containing the bleaching agent is first prepared. The aqueous solution containing the bleaching agent may be prepared using household bleach (e.g., Clorox® bleach) or other suitable source of chlorine-containing bleaching agent or other bleaching agent. The bleaching agent solution is then combined with the ORP water solution.

The bleaching agent may be added to the ORP water solution in any suitable amount. Preferably, the ORP water solution containing a bleaching agent is non-irritating to human or animal skin. Preferably, the total chloride ion content of the ORP water solution containing a chlorine-containing bleaching agent is from about 1000 ppm to about 5000 ppm, and preferably from about 1000 ppm to about 3000 ppm. The pH of the ORP water solution containing a chlorine-containing bleaching agent is preferably from about 8 to about 10, and the oxidative-reductive potential is from about +700 mV to about +800 mV.

The ORP water solution may optionally contain additives suitable for the household and workplace cleaning environment. Suitable additives include surfactants, such as detergents and cleaning agents. Perfumes or other scent-producing compounds may also be included to enhance consumer reception of the ORP water solution.

The present invention further provides a process for producing an ORP water solution using at least one electrolysis cell comprising an anode chamber, cathode chamber and salt solution chamber located between the anode and cathode chambers, wherein the ORP water solution comprises anode water and cathode water. A diagram of a typical three chamber electrolysis cell useful in the invention is shown in FIG. 1.

The electrolysis cell 100 has an anode chamber 102, cathode chamber 104 and salt solution chamber 106. The salt solution chamber is located between the anode chamber 102 and cathode chamber 104. The anode chamber 102 has an inlet 108 and outlet 110 to permit the flow of water through the anode chamber 100. The cathode chamber 104 similarly has an inlet 112 and outlet 114 to permit the flow of water through the cathode chamber 104. The salt solution chamber 106 has an inlet 116 and outlet 118. The electrolysis cell 100 preferably includes a housing to hold all of the components together.

The anode chamber 102 is separated from the salt solution chamber by an anode electrode 120 and an anion ion exchange membrane 122. The anode electrode 120 may be positioned adjacent to the anode chamber 102 with the membrane 122 located between the anode electrode 120 and the salt solution chamber 106. Alternatively, the membrane 122 may be positioned adjacent to the anode chamber 102 with the anode electrode 120 located between the membrane 122 and the salt solution chamber 106.

The cathode chamber 104 is separated from the salt solution chamber by a cathode electrode 124 and a cathode ion exchange membrane 126. The cathode electrode 124 may be positioned adjacent to the cathode chamber 104 with the membrane 126 located between the cathode electrode 124 and the salt solution chamber 106. Alternatively, the membrane 126 may be positioned adjacent to the cathode chamber 104 with the cathode electrode 124 located between the membrane 126 and the salt solution chamber 106.

The electrodes are generally constructed of metal to permit a voltage potential to be applied between the anode chamber and cathode chamber. The metal electrodes are generally planar and have similar dimensions and cross-sectional surface area to that of the ion exchange membranes. The electrodes are configured to expose a substantial portion of the surface of the ion exchange members to the water in their respective anode chamber and cathode chamber. This permits the migration of ionic species between the salt solution chamber, anode chamber and cathode chamber. Preferably, the electrodes have a plurality of passages or apertures evenly spaced across the surface of the electrodes.

A source of electrical potential is connected to the anode electrode 120 and cathode electrode 124 so as to induce an oxidation reaction in the anode chamber 102 and a reduction reaction in the cathode chamber 104.

The ion exchange membranes 122 and 126 used in the electrolysis cell 100 may be constructed of any suitable material to permit the exchange of ions between the salt solution chamber 106 and the anode chamber 102 such as chloride ions (Cl$^-$) and between the salt solution salt solution chamber 106 and the cathode chamber 104 such as sodium ions (Na$^+$). The anode ion exchange membrane 122 and cathode ion exchange membrane 126 may be made of the same or different material of construction. Preferably, the anode ion exchange membrane comprises a fluorinated polymer. Suitable fluorinated polymers include, for example, perfluorosulfonic acid polymers and copolymers such as perfluorosulfonic acid/PTFE copolymers and perfluorosulfonic acid/TFE copolymers. The ion exchange membrane may be constructed of a single layer of material or multiple layers.

The source of the water for the anode chamber 102 and cathode chamber 104 of the electrolysis cell 100 may be any suitable water supply. The water may be from a municipal water supply or alternatively pretreated prior to use in the electrolysis cell. Preferably, the pretreated water is selected from the group consisting of softened water, purified water, distilled water, and deionized water. More preferably, the pretreated water source is ultrapure water obtained using reverse osmosis purification equipment.

The salt water solution for use in the salt water chamber 106 may be any aqueous salt solution that contains suitable ionic species to produce the ORP water solution. Preferably, the salt water solution is an aqueous sodium chloride (NaCl) salt solution, also commonly referred to as a saline solution. Other suitable salt solutions include other chloride salts such as potassium chloride, ammonium chloride and magnesium chloride as well as other halogen salts such as potassium and bromine salts. The salt solution may contain a mixture of salts.

The salt solution may have any suitable concentration. The salt solution may be saturated or concentrated. Preferably, the salt solution is a saturated sodium chloride solution.

Figure 2:
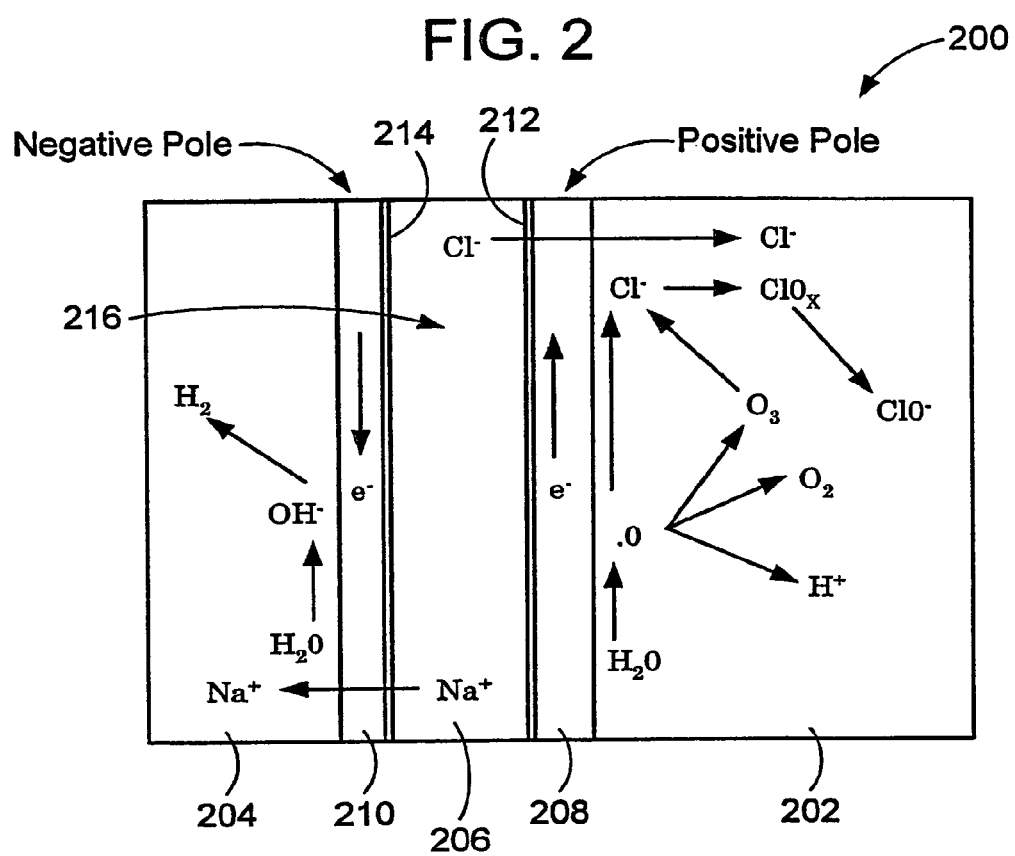
FIG. 2 illustrates a three-chambered electrolysis cell and depicts ionic species generated therein.

The various ionic species produced in the three chambered electrolysis cell useful in the invention are illustrated in FIG. 2. The three chambered electrolysis cell 200 includes an anode chamber 202, cathode chamber 204, and a salt solution chamber 206. Upon application of a suitable electrical current to the anode 208 and cathode 210, the ions present in the salt solution flowing through the salt solution chamber 206 migrate through the anode ion exchange membrane 212 and cathode ion exchange membrane 214 into the water flowing through the anode chamber 202 and cathode chamber 204, respectively.

Positive ions migrate from the salt solution 216 flowing through the salt solution chamber 206 to the cathode water 218 flowing through the cathode chamber 204. Negative ions migrate from the salt solution 216 flowing through the salt solution chamber 206 to the anode water 220 flowing through the anode chamber 202.

Preferably, the salt solution 216 is aqueous sodium chloride (NaCl) that contains both sodium ions (Na$^+$) and chloride ions (Cl$^-$) ions. Positive Na$^+$ ions migrate from the salt solution 216 to the cathode water 218. Negative Cl$^-$ ions migrate from the salt solution 216 to the anode water 220.

The sodium ions and chloride ions may undergo further reaction in the anode chamber 202 and cathode chamber 204. For example, chloride ions can react with various oxygen ions and other species (e.g., oxygen free radicals, $O_2$, $O_3$) present in the anode water 220 to produce ClOn- and ClO$^-$. Other reactions may also take place in the anode chamber 202 including the formation of oxygen free radicals, hydrogen ions (H$^+$), oxygen (as $O_2$), ozone ($O_3$), and peroxides. In the cathode chamber 204, hydrogen gas ($H_2$), sodium hydroxide (NaOH), hydroxide ions (OH$^-$), ClOn- ions, and other radicals may be formed.

Figure 3:
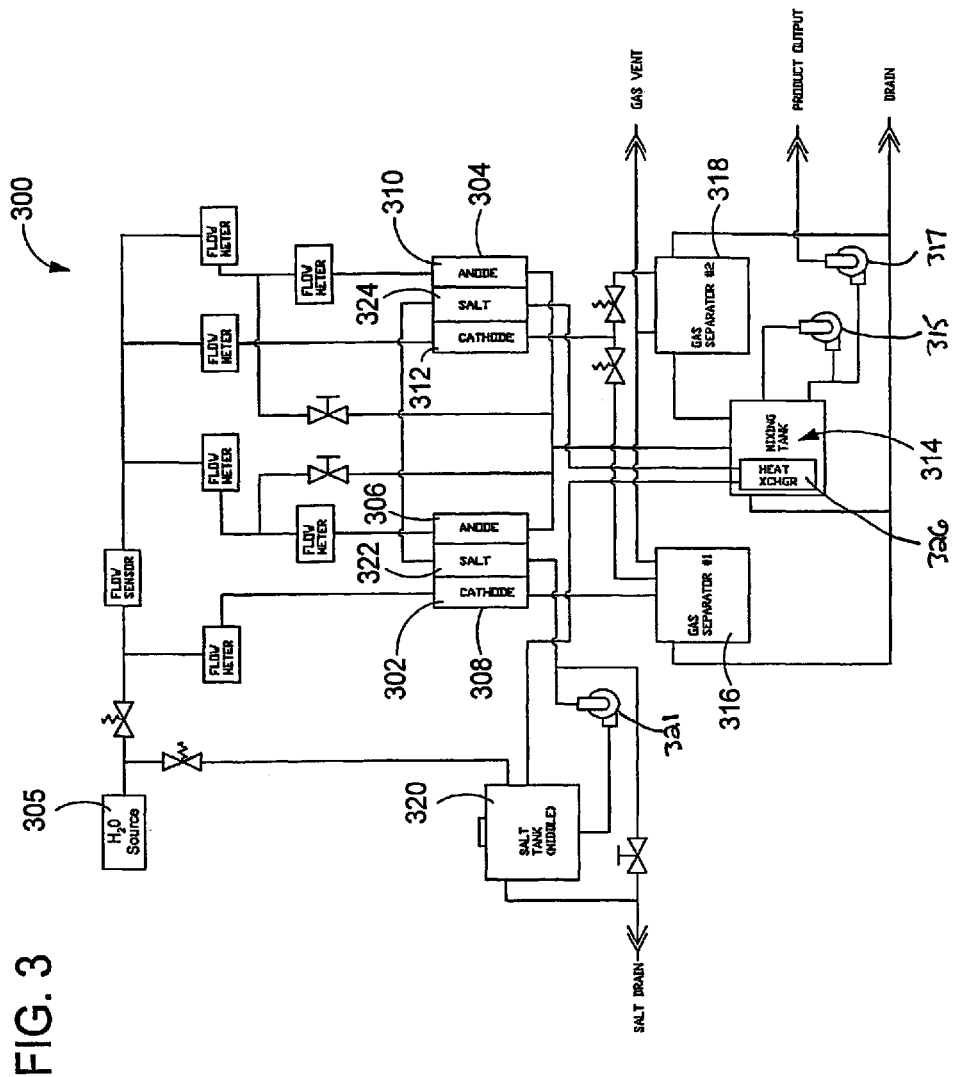
FIG. 3 is a schematic flow diagram of a process for producing an oxidative reductive potential water of the present invention.

The invention further provides for a process and apparatus for producing an ORP water solution using at least two three chambered electrolysis cells. A diagram of a process for producing an ORP water solution using two electrolysis cells of the invention is shown in FIG. 3.

The process 300 includes two three-chambered electrolytic cells, specifically a first electrolytic cell 302 and second electrolytic cell 304. Water is transferred, pumped or otherwise dispensed from the water source 305 to anode chamber 306 and cathode chamber 308 of the first electrolytic cell 302 and to anode chamber 310 and cathode chamber 312 of the second electrolytic cell 304. Typically, the process of the invention can produce from about 1 liter/minute to about 50 liters/minute of ORP water solution. The production capacity may be increased by using additional electrolytic cells. For example, three, four, five, six, seven, eight, nine, ten or more three-chambered electrolytic cells may be used to in increase the output of the ORP water solution of the invention.

The anode water produced in the anode chamber 306 and anode chamber 310 is collected are collected in the mixing tank 314. A portion of the cathode water produced in the cathode chamber 308 and cathode chamber 312 is collected in mixing tank 314 and combined with the anode water. The remaining portion of cathode water produced in the process is discarded. The cathode water may optionally be subjected to gas separator 316 and/or gas separator 318 prior to addition to the mixing tank 314. The gas separators remove gases such as hydrogen gas that are formed in cathode water during the production process.

The mixing tank 314 may optionally be connected to a recirculation pump 315 to permit homogenous mixing of the anode water and portion of cathode water from electrolysis cells 302 and 304. Further, the mixing tank 314 may optionally include suitable devices for monitoring the level and pH of the ORP water solution. The ORP water solution may be transferred from the mixing tank 314 via pump 317 for application in disinfection or sterilization at or near the location of the mixing tank. Alternatively, the ORP water solution may be dispensed into suitable containers for shipment to a remote site (e.g., warehouse, hospital, etc.).

The process 300 further includes a salt solution recirculation system to provide the salt solution to salt solution chamber 322 of the first electrolytic cell 302 and the salt solution chamber 324 of the second electrolytic cell 304. The salt solution is prepared in the salt tank 320. The salt is transferred via pump 321 to the salt solution chambers 322 and 324. Preferably, the salt solution flows in series through salt solution chamber 322 first followed by salt solution chamber 324. Alternatively, the salt solution may be pumped to both salt solution chambers simultaneously.

Before returning to the salt tank 320, the salt solution may flow through a heat exchanger 326 in the mixing tank 314 to control the temperature of the ORP water solution as needed.

The ions present in the salt solution are depleted over time in the first electrolytic cell 302 and second electrolytic cell 304. An additional source of ions may periodically be added to the mixing tank 320 to replace the ions that are transferred to the anode water and cathode water. The additional source of ions may be used to maintain a constant pH of the salt solution which tends to drop (i.e., become acidic) over time. The source of additional ions may be any suitable compound including, for example, salts such as sodium chloride. Preferably, sodium hydroxide is added to the mixing tank 320 to replace the sodium ions (Na$^+$) that are transferred to the anode water and cathode water.

In another embodiment, the invention provides an apparatus for producing an oxidative reductive potential water solution comprising at least two three-chambered electrolytic cells. Each of the electrolytic cells includes an anode chamber, cathode chamber, and salt solution chamber separating the anode and cathode chambers. The apparatus includes a mixing tank for collecting the anode water produced by the electrolytic cells and a portion of the cathode water produced by one or more of the electrolytic cells. Preferably, the apparatus further includes a salt recirculation system to permit recycling of the salt solution supplied to the salt solution chambers of the electrolytic cells.

The following examples further illustrate the invention but, of course, should not be construed as in any way limiting in its scope.

EXAMPLES 1-3

These examples demonstrate the unique features of the ORP water solution of the invention. The samples of the ORP water solution in Examples 1-3 were analyzed in accordance with the methods described herein to determine the physical properties and levels of ionic and other chemical species present in each sample. The pH, oxidative-reductive potential (ORP) and ionic species present are set forth in Table 1 for each sample of the ORP water solution.

TABLE 1

Physical characteristics and ion species present for the ORP water solution samples

|  | EXAMPLE 1 | EXAMPLE 2 | EXAMPLE 3 |
|---|---|---|---|
| pH | 7.45 | 7.44 | 7.45 |
| ORP (mV) | +879 | +881 | +874 |
| Total Cl$^-$ (ppm) | 110 | 110 | 120 |
| Bound Cl$^-$ (ppm) | 5 | 6 | 6 |
| Cl Dioxide (ppm) | 1.51 | 1.49 | 1.58 |
| Ozone | 0.12 | 0.10 | 0.12 |
| Hydrogen Peroxide | 42.5 | 43.0 | 42.0 |

As demonstrated by these results, the present invention provides a ORP water solution having suitable physical characteristics for use in disinfection, sterilization and/or cleaning.

EXAMPLES 4-10

These examples demonstrate the addition of a bleaching agent to the ORP water solution according to the invention in various amounts. In particular, these examples demonstrate the antimicrobial activity and fabric bleaching ability of the compositions.

A 10% Clorox® bleach solution was prepared using distilled water. The following solutions were then prepared using the 10% bleach solution: 80% ORP water solution/20% bleach (Example 4); 60% ORP water solution/40% bleach (Example 5); 40% ORP water solution/60% bleach (Example 6); 20% ORP water solution/80% bleach (Example 7); and 0% ORP water solution/100% bleach (Example 8). Two control solutions were also used for comparison including 100% ORP water solution/0% bleach (Example 9) and an ORP water solution with 0.01% Tween 20 detergent (Example 10). The physical characteristics of these samples were determined, specifically pH, oxidative-reductive potential (ORP), total chlorine (Cl$^-$) content, hypochlorous acid (HClO$^-$) content, chlorine dioxide content and peroxide content, and are set forth in Table 2.

TABLE 2

Physical characteristics of ORP water solution/bleach compositions

|  | pH | ORP | Total Cl$^-$ (ppm) | HClO$^-$ (ppm) | Cl Dioxide (ppm) | Peroxide (ppm) |
|---|---|---|---|---|---|---|
| Ex. 4 | 8.92 | +789 | 1248 | 62 | n.d. | n.d. |
| Ex. 5 | 9.20 | +782 | 2610 | 104 | n.d. | n.d. |
| Ex. 6 | 9.69 | +743 | 4006 | 80 | n.d. | n.d. |
| Ex. 7 | 9.86 | +730 | 4800 | 48 | n.d. | n.d. |
| Ex. 8 | 9.80 | +737 | 5000 | 50 | n.d. | n.d. |
| Ex. 9 | 7.06 | +901 | 64 | 32 | 2.8 | 35 |
| Ex. 10 | 6.86 | +914 | 51 | 26 | 2.7 | 35 |

The large bolus of chlorine ions added as part of the bleaching agent prevented the accurate measurement of the chlorine dioxide and peroxide levels as indicated with the n.d. designations. As these examples demonstrate, the hypochlorous acid levels of the ORP water solution with and without the addition of a bleaching agent are similar.

The samples of Examples 4-10 were subjected to a high spore count test using *Bacillus subtilis* var. *niger* spores (ATCC #9372 obtained from SPS Medical of Rush, N.Y.). Spore suspensions were concentrated (by evaporation in a sterile hood) to 4×10$^6$ spores per 100 microliters. A 100 microliter sample of the spore suspension were mixed with 900 microliters of each of the samples in Examples 4-10. The samples were incubated at room temperature for periods of 1 to 5 minutes as set forth in Table 3. At the indicated times, 100 microliters of the incubated samples were plated onto individual TSA plates and incubated for 24 hours at 35° C.±2° C., after which the number of resulting colonies on each plate was determined. The control plates demonstrated that the starting spore concentrations were >1×10$^6$ spores/100 microliters. The concentration of *Bacillus* spores for the various samples at the various incubation times (as the average of two determinations) is set forth in Table 3.

TABLE 3

*Bacillus* spore concentrations

|  | 1 minute | 2 minutes | 3 minutes | 4 minutes | 5 minutes |
|---|---|---|---|---|---|
| Ex. 4 | >>1000 | 411 | 1 | 0 | 2 |
| Ex. 5 | >>1000 | 1000 | 1 | 0 | 0 |
| Ex. 6 | >>1000 | >>1000 | >1000 | 22 | 0 |
| Ex. 7 | >>1000 | >>1000 | >1000 | 15 | 0 |
| Ex. 8 | >>1000 | >>1000 | >1000 | 3 | 1 |
| Ex. 9 | >>1000 | 74 | 0 | 0 | 0 |
| Ex. 10 | >>1000 | 239 | 3 | 0 | 0 |

As these results demonstrate, as the concentration of bleach (as 10% aqueous bleach solution) increases, the amount of *Bacillus* spores killed is reduced for the samples incubated for 2-3 minutes. However, for samples incubated for 5 minutes, the bleach concentration does not impact *Bacillus* spore kill. Further, the results demonstrate that the addition of 0.01% detergent to the ORP water solution does not reduce spore kill.

The samples of Examples 4-10 were subjected to a fabric bleaching test. The fabric upon which the samples were tested was a 100% rayon children's t-shirt with dark blue dye patches. Two inch square pieces of dyed fabric were placed into 50 mL plastic tubes. Each fabric piece was covered by a sample of the solution in Examples 4-10. The elapsed time until complete bleaching was obtained, as determined by the whitening of the fabric, is set forth in Table 4.

TABLE 4

Time until complete bleaching of fabric sample

| Example | Time |
|---------|------|
| Ex. 4   | 39 minutes |
| Ex. 5   | 23 minutes |
| Ex. 6   | 18 minutes |
| Ex. 7   | 19 minutes |
| Ex. 8   | 10 minutes |
| Ex. 9   | >6 hours |
| Ex. 10  | >6 hours |

As demonstrated by these examples, as the concentration of the ORP water solution increases in the composition, the time until complete bleaching is achieved increases.

EXAMPLE 11

This example relates to the toxicological profile of on an ORP water solution of the present invention. Microcyn 60 (or M60), an exemplary ORP water solution of the present invention, was used in these studies.

In terms of safety, M60 was not an irritant to the skin or conjuctiva of rabbits as tested in compliance with international standards (AAMI 1997; NV SOP 16G-44; PFEUM 2000). Furthermore, an acute inhalation toxicity study in rats demonstrated that administration of Microcyn 60 by this route is safe.

The potential irritant effects of Microcyn 60 were evaluated in a primary ocular irritation study in rabbits. A volume of 0.1 mL of Microcyn 60 was instilled in the right eye of three New Zealand white rabbits. The left eye of each animal was left untreated as a control. The eyes were observed and scored at 1, 24, 48 and 72 hours for corneal ulceration or opacity, inflammation of the iris, and redness or chemosis of the conjunctiva. All animals were also observed once daily for mortality and signs of ill health.

No signs of ocular irritation were observed in any of the treated or control eyes at any time during the study. All animals appeared clinically healthy for the duration of the study. These findings indicate that Microcyn 60 does not cause a positive irritation response.

An acute inhalation toxicity study was also performed in rats to determine the potential inhalation toxicity of Microcyn 60. Ten Sprauge-Dawley albino rats were exposed to an aerosol generated from undiluted Microcyn 60 for 4 hours. The concentration of the Microcyn 60 was determined to be 2.16 mg/L. All animals were observed frequently on the day of exposure and once daily for 14 days thereafter for mortality and clinical/behavioral signs of toxicity. All animals were euthanized on Day 14 and gross necropsies were performed.

All animals showed very slight to slight piloerection and very slight decreased activity at 4½ and 6 hours after exposure began but were asymptomatic by the following day and appeared clinically normal for the duration of the study. One male failed to gain weight between Day 0 and Day 7. There was no mortality and the gross necropsies revealed no observable abnormalities. The estimated acute inhalation LD50 from this study is greater than 2.16 mg/L.

Additional toxicological studies were performed in the rabbit. Aerosol superoxidized water (1 mL) will be delivered to the right nostril via a positive-pressure device to 20 New Zeland rabbits, three times a day for 15, 30, 45 and 60 days. The left-control nostril will be left without any treatment. Nasomucosa biopsies from the non treated- and M60 treated-nostrils will be obtained from five animals at each time point. These tissues will then be observed under optical and electron microscopy. A complete medical exam will be conducted in each animal every other day to document nasal obstruction, facial pain, pressure, mucopurulent rhinorrhea, and malaise. Side effects will be reported as infrequent, mild, and transient.

Changes to the nasal mucosa appeared after applying intranasal M60 for 60 days. There was mild destruction of the epithelia, discrete inflammatory infiltration of the sub-epithelia region and hyperplasia of glands and blood vessels in all samples on day 60. Under ultrastructral observation, we found that varying cyst-like changes within epithelial cells appeared; the mitochondria were condensed and deformed and part of the membrane was dissolved. Some epithelial cells were detached; epithelial cilia almost disappeared, and its membrane was dissolved and intercellular spaces were widened. Some cells had detached from the basement membrane. The tunica propria was mildly edematous.

This study demonstrates that M60 can mildly irritate the nasal mucosa after intranasal administration for sixty days. However, this damage was minimum and reversible, so the intranasal route of M60 administration could be considered safe. This is based on the fact that although the nasal mucosa can be seriously injured after applying vasoconstrictors for several years, it is still restored to normal after stopping these drugs. This is possible due to the process of regeneration in the nasal mucosa that depends on whether the basal cells and basement membrane remain intact after injury. Neighboring basal cells can move to the lesion along the basement membrane and cover the lesion. Therefore, even in the presence of mild detachment of the epithelial cells in some regions after M60 treatment, the basement membrane survived, and the surviving epithelial cells near the pathological region grew toward the region lacking the epithelia. Furthermore, topical steroids could have also been applied to promote recovery of the structure and function of the nasal mucosa.

In conclusion, M60 intranasal administration for five days was safe in this cohort. Pathological mucosa changes were mild and reversible. Therefore, the intranasal administration of M60 could be widely used.

EXAMPLE 12

This example describes the reduced blood loss experienced in oral and maxillofacial procedures when using ORP water or ORP water in gel form.

A comparative study of 60 patients was conducted—56 were oral surgery patients and 4 underwent major maxillofacial procedures. The two study groups consisted of Group A—treated with comprehensive care, conventional disinfectants and antibiotics—and Group B—treated with comprehensive care and ORP water without antibiotics. The test data is summarized it Table 5.

TABLE 5

| End Points | Group A (control) | Group B (ORP water) |
|------------|-------------------|---------------------|
| Blood loss (cc) | 900-1200 | 500-600 |
| Alveolitis with Antibiotics (% patients) | 3.4% | 0 |

TABLE 5-continued

| End Points | Group A (control) | Group B (ORP water) |
|---|---|---|
| Alveolitis without Antibiotics (% patients) | 34% | 0 |
| Post-operative infections (% patients) | 2.8% | 0 |

This study indicates that Group B (treated with ORP water) had an absence of infection and alveolitis, and fewer post-operative infections and reduced blood loss compared to the control group.

EXAMPLE 13

This example illustrates a clinical study, which can be used to determine the effectiveness of an ORP water solution of the present invention for treating pharyngitis.

One such ORP water solution for use in this study is known as "Estericide," recently introduced on the Mexican market as an antiseptic. Estericide is a superoxidized solution of neutral pH with germicidal, sterilizing and wound antiseptic activity in accordance with certifications obtained from the Secretariat of Health of Mexico. Estericide is prepared from pure water and salt (NaCl), has a small concentration of sodium (<55 ppm) and chlorine (<80 ppm), a pH in the range of 7.2 to 7.8, and oxidation-reduction potential in the range of 840 mV to 960 mV. Estericide is produced in one concentration only, and need not be activated or diluted.

This solution is produced from water obtained by reverse osmosis, which is then subjected to an electrochemical gradient generated by high voltage and sodium chloride. In this way, the reactive species that form in the multiple chambers where the electrochemical gradient is generated are selected in a controlled way to create Estericide. The result is a solution with a controlled content of free radicals that confer a high oxidation-reduction potential (+840 mV to +960 mV) and consequently high antimicrobial activity.

Hypochlorous acid and sodium hypochlorite are the most abundant elements contained in Estericide, with others in minor concentration, such as hydrogen peroxide, ozone, chloride ions, hydride and sodium hydroxide, among others. Although applicants do not wish to be bound by a particular theory, it is believed that the disinfectant effect does not necessarily depend on the quantity of chlorine, but rather, in the content of free radicals, since the levels of sodium and chlorine in Estericide are less than 50 and 60 parts per million, respectively. Also, and in contrast to other superoxidized solutions that have been reported in the literature, Estericide has a neutral pH (6.4-7.8), is not corrosive and is stable in storage up to 2 years. All these characteristics have made it possible to produce a superoxidized solution that is effective as a high-level disinfectant and compatible for use both on inanimate surfaces and in tissues.

Accelerated stability tests have demonstrated that Estericide can be stored in widely varying temperature conditions, from 4 to 65° C., without losing its disinfectant activity for a period of 2 years. This property of prolonged stability on the shelf is also the difference from superoxidized solutions reported previously that are only effective if they are used immediately after being produced. In other words, while Estericide can be stored and distributed even in extreme conditions without losing its antimicrobial activity, other solutions would have to be produced by a specialized and costly machine in every hospital that tried to use that solution. Nevertheless, the manufacturer recommends that, once the container of Estericide is opened, it be used within 30 days for the purpose of guaranteeing uniform activity and consistent results.

Because Estericide is produced in only one concentration, the dose of Estericide can be changed only by changes in the volume applied per unit area of the skin. In the toxicological studies, the doses of Estericide applied topically to the intact skin varied between 0.05 and 0.07 mL/cm$^2$; in the study of acute dermatological toxicity and in the investigation of skin irritation, they were up to 8.0 mL/cm$^2$, and in those that investigated its application in deep wounds, Estericide was applied in a dose of 0.09 mL/cm$^2$.

Toxicological studies were carried out that applied Estericide topically to the intact skin, using a single application with exposure of 4 to 24 h. Multiple applications of Estericide, one or two times a day, during a period of 7 days were assessed for deep wounds in rats.

Two studies were carried out on the intact skin of rabbits to evaluate the effect of Estericide as to acute irritation and dermal toxicity. No clinical signs, dermal irritation, or abnormalities in the skin at autopsy were found in any of the animals exposed to Estericide.

The characterization of local and systemic toxicity from topically applied Estericide to a deep wound was evaluated in rats. No abnormalities, significant differences in the parameters of the blood chemistry or hematic cytology were observed, nor anomalies in the autopsies. The skin irritation gradings and the histopathology of the wounds and the tissues around the place of application did not reveal any difference between the wounds treated with Estericide and those of the control group treated with saline solution.

The systemic toxicity of Estericide was also evaluated by means of an intraperitoneal injection in mice. For this, five mice were injected with a single dose (50 mL/kg) of Estericide by the intraperitoneal route. In the same way, five control mice were injected with a single dose (50 mL/kg) of saline solution (sodium chloride at 0.9%). In this investigation, neither mortality nor any evidence of systemic toxicity was observed in any of the animals that received the single intraperitoneal dose of Estericide, for which the $LD_{50}$ is above 50 mL/kg.

Estericide was administered by the oral route to rats to allow its absorption and to characterize any inherent toxic effect of the product. For this a single dose (4.98 mL/kg) was administered by esophageal tube to three albino rats of the Sprague-Dawley strain. There was no mortality, nor were there clinical signs or abnormalities in the autopsies of any of the animals exposed to the single oral dose of Estericide.

The potential of topically applied Estericide for ocular irritation was also evaluated in rabbits. Ocular irritation was not observed nor any other clinical sign in any animal exposed to Estericide by topical administration through the ocular route.

Estericide was applied by the inhalatory route to rats to determine potential acute toxicity by inhalation. All the animals showed a very slight or slight reduction in activity and piloerection after the exposure, but they were all asymptomatic on the following day. Mortality or abnormalities were not observed at autopsy of the animals exposed to Estericide by inhalation.

Evaluation of the potential for sensitization of the skin with Estericide was carried out in guinea pigs using a modified occlusion patch method (Buehler). Irritation was not observed in the animals of the control group after a simple treatment challenge, nor in the animals evaluated (treated by induction) after challenge with the treatment. Therefore, Estericide does not provoke a sensitizing reaction.

Thus, when it has been applied to the intact skin, deep open dermal wounds, in the conjunctival sac, by oral and inhalation routes or by means of intraperitoneal injection, Estericide has not shown adverse effects related to the product. There is also experience in having treated more than 500 patients with wounds of very diverse nature in the skin and mucosae, with excellent antiseptic and cosmetic results. Accordingly, topically applied Estericide should be effective and well-tolerated in this clinical trial.

Estericide is packaged in transparent 240 mL PET bottles. This product is stored at ambient temperature and remains stable for up to 2 years on the shelf if the bottle is not opened. On having been opened, it is recommended that all of the product be used in less than 90 days. From its profile of high biological safety, Estericide can be emptied into the sink without risk of contamination or corrosion.

Multiple microbial trials have been run with Estericide, both in the United States and in Mexico. Eradication of more than 90% of the bacteria occurs in the first few seconds of exposure. The antibacterial and antimycotic activity that Estericide exhibits in accordance with this standard is summarized in Table 6.

TABLE 6

| Bacterium | Catalog | Time of action (reduction below 99.999%) |
|---|---|---|
| Ps. aeruginosa | ATCC 25619 | 1 min |
| St. aureus | ATCC 6538 | 1 min |
| E. coli | ATCC 11229 | 1 min |
| S. typhi | CDC 99 | 1 min |
| C. albicans | ATCC | 1 min |
| B. subtilis | 9372 | |
| Low spore ($10^4$) | | 10 min |
| High spore ($10^6$) | | 15 min |

The sporicidal activity trial was carried out in accordance with the PAHO [Pan-American Health Organization]/WHO protocol.

As for the virucidal activity, Estericide was found to reduce the viral load of human immunodeficiency virus (strain SF33) by more than 3 logs in five minutes. This was verified by the absence of cytopathic effect and of the antigen Agp24 in the trials of virus treated with Estericide. These trials were undertaken in accordance with the virucide protocols of the United States Environmental Protection Agency (DIS/TSS-7/Nov. 12, 1981).

The virucidal activity of Estericide has recently been confirmed in studies carried out in the United States against HIV and polio virus, and its activity against *Listeria monocytogenes*, MRSA and *Mycobacterium tuberculosis* has also been documented. Thus, it has been demonstrated that Estericide, when it is administered as recommended, can eradicate bacteria, fungi, viruses and spores from one to fifteen minutes of exposure.

In this clinical study, 40 patients with acute pharyngitis/tonsillitis caused by group A β-hemolytic *Streptococcus* and who have not received treatment are recruited. The inclusion criteria are as follows: age 12 to 40 years and two or more of the following symptoms: oropharyngeal burning; pain on swallowing; pharyngeal erythema or of the tonsils (with or without exudate); cervical lymphadenopathy; and positive immunoassay for group A *Streptococcus* antigen (StrepA Test-Abbott Labs). The exclusion criteria are as follows: fever >38° C.; bronchospasm (excluded by the clinic); severe cough; sinusitis-rhinitis (excluded by the clinic); esophageal reflux (excluded by the clinic); use of antibiotics in the two weeks prior to the study; patients who have taken part in another clinical study in the last 8 weeks; rheumatic fever; poststreptococcal glomerulonephritis; severe chronic cardiopathy; severe renal, hepatic or pulmonary insufficiencies; and pregnancy or lactation.

At the beginning of the study, patients may use such concomitant medicines as antipyretics and analgesics, including paracetamol and acetylsalicylics but not anti-inflammatories such as ibuprofen, Mesulid, COX-2 inhibitors, or steroids. Written informed consent must be obtained before the patient submits to any specific procedure of the study.

The patients are evaluated in three visits. In the first visit, the patient clinically presents acute pharyngitis/tonsillitis, and the clinical history is taken, and a medical examination, rapid immunoassay for *Streptococcus*, and taking of a pharyngeal exudate is carried out. After being declared eligible and after having signed the letter of informed consent, the patient is prescribed two oropharyngeal cleansings of 30 sec and 5 mL Estericide each. These rinsings are done every 3 h for a total of four times a day for 3 days.

The second is made 72 h after having been treated with Estericide. In the second visit, the clinical evolution and side effects of Estericide are evaluated. A new pharyngeal exudate is taken, and it will be decided, in accordance with the clinical evolution, if the continuing treatment will be with antibiotics or a palliative. A third visit is done after 10 days to discharge the patient.

To be eligible and clinically evaluated in this study, each patient must present A β-hemolytic *Streptococcus* pharyngitis/tonsillitis confirmed by culture. All the patients must comply with 18 rinsings of 30 sec and 5 mL of Estericide each, or a maximum of 24 rinsings in the space of 72 h.

The primary parameter of efficacy is a reduction by 3 orders of magnitude in the bacterial load of the initial culture compared to the culture taken after the administration of Estericide. This bacteriological evaluation is realized 72 h after treatment with Estericide. Secondary parameters of efficacy are the improvement reported clinically, with particular emphasis on the reduction of pharyngeal pain and dysphagia. Clinical symptoms are reported in visits 1, 2 and 3.

Tolerance is evaluated by reports of adverse events. An adverse event is defined as any symptomatic declaration of the patient who submits to the treatment with Estericide, related or not to the antiseptic, that appears in the course of the treatment.

The results of bacteriological efficacy (the principal criterion of efficacy) are issued by a bacteriologist independently of the clinical symptoms. The tests for the group A *Streptococcus* antigen and the initial pharyngeal exudate culture are done in the first visit (Visit 1), in accordance with the Schedule of Evaluations and before the administration of Estericide. The second taking and culture of pharyngeal exudate is carried out 72 h after the administration of Estericide (Visit 2). An antibiogram is done on all the cultures to determine the bacterial resistance to penicillin, erythromycin, clarithromycin and lincomycin by means of the standard diffusion disc test. Bacteriological efficacy is defined as the reduction by three orders of magnitude of the bacterial count between the initial culture and the culture taken 72 h after administering Estericide.

Bacteriological failure is indicated by a reduction of less than three orders of magnitude of the bacterial count in the culture at 72 h posttreatment. Indeterminate responses are documented in those cases in which the transport of the sample has been delayed for more than 48 h, in those cases in which the swab has not been immersed in the transport medium, or in those cases in which the sample has been lost. These cases are outside the analysis of the study and are replaced by new cases until those of forty eligible patients have been completed.

The follow-up and reporting phase begins when the patient finishes the administration of Estericide, and from the second visit. In this evaluation, according to the clinical evolution and the presence of possible adverse effects, the patients are categorized as follows:

Therapeutic failures if their initial signs and symptoms have not been eliminated or if there is worsening of their general condition with systemic symptoms. In these cases an oral antibiotic is prescribed, such as procaine penicillin, clarithromycin or azithromycin at the dose and for the time that the treating doctor indicates, and they are evaluated in one week.

Clinically cured if the symptoms and signs that were present in Visit 1 have been eliminated. In these cases in which the acute process is resolved, the patient is discharged and reported as clinically cured. In any case, the patient is asked to return for a third check-up visit in one week.

Indeterminate evolution. The evolution of any patient who could not have been evaluated clinically for any good reason; for example, a coinfection, or if the evaluation was done very late, later than 72 h. In these cases, the patients is still able to be included in the analysis of the study provided it is possible to document the result of the pharyngeal exudate and culture at 72 h.

The statistical analysis used in this clinical study takes into account all the patients who have received at least 18 rinsings of Estericide of 30 sec each in a period of 72 h. This same criterion is considered to include any patient in the analysis of tolerance. The principal criterion for analysis of efficacy is the reduction of the bacterial count of β-hemolytic *Streptococcus* by three orders of magnitude in the culture carried out at 72 h posttreatment with Estericide. The statistical analysis is realized by means of a Wilcoxon paired samples test. Statistical analysis of the clinical variables is realized using the ANOVA test for quantitative variables. The minimal evaluable number of patients is 30 patients.

An adverse event is any contrary medical occurrence in a patient or subject of clinical investigation to whom a pharmaceutical product is administered and that does not necessarily have a causal relationship with that medicine. An adverse event can, therefore, be any unfavorable and unintended sign (including an abnormal laboratory finding), symptom or illness temporarily associated with the use of a medical product, whether it is considered to be related to this use or not. Preexisting conditions that deteriorate during a study are reported as adverse events.

The treatment is suspended at any time during the 72 h of duration in case of adverse events that are moderate to severe in intensity. Subsequent treatment is determined by the treating doctor. In accordance with this example, the effectiveness of an ORP water solution of the present invention for treating sinusitis is thus demonstrated.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating sinusitis in a patient, the method comprising administering to the patient a therapeutically effective amount of an oxidative reductive potential water solution, wherein the solution is stable for at least about two months and the solution has a pH of from about 6.4 to about 7.8, wherein the sinusitis results from an infection by one or more bacteria.

2. The method of claim 1, comprising administering the oxidative reductive potential water solution to the upper respiratory airway.

3. The method of claim 1, comprising delivering the oxidative reductive potential water solution in the form of a liquid.

4. The method of claim 1, wherein the sinusitis is acute sinusitis.

5. The method of claim 1, wherein the sinusitis further results from a fungal infection.

6. The method of claim 5, wherein the fungal infection is by one or more fungi selected from the group of *zygomycetes, aspergillus*, and *candida*.

7. The method of claim 1, wherein the sinusitis further results from an allergic reaction.

8. The method of claim 7, wherein the allergic reaction is caused by dust, mold, pollen, or a combination thereof.

9. The method of claim 1, wherein the pH of the oxidative reductive potential water solution is from about 7.4 to about 7.6.

10. The method of claim 1, wherein the oxidative reductive potential water solution comprises from about 10% by volume to about 50% by volume of cathode water and from about 50% by volume to about 90% by volume of anode water.

11. The method of claim 1, wherein the oxidative reductive potential water solution comprises a free chlorine species comprising hypochlorous acid, a hypochlorite ion, sodium hypochlorite, chlorite ion, or a combination or two or more of any of these.

12. The method of claim 1, wherein the oxidative reductive potential water solution comprises from about 15 ppm to about 35 ppm hypochlorous acid.

13. The method of claim 1, wherein the oxidative reductive potential water solution comprises from about 25 ppm to about 50 ppm sodium hypochlorite.

14. The method of claim 1, wherein the oxidative reductive potential water solution comprises from about 15 ppm to about 35 ppm hypochlorous acid, and from about 25 ppm to about 50 ppm sodium hypochlorite.

15. The method of claim 1, further comprising administering an additional therapeutic agent comprising an antihistamine, decongestant, anti-infective agent, anti-inflammatory agent, or a combination of two or more of any of these.

16. The method of claim 1, wherein the sinusitis is chronic sinusitis.

17. The method of claim 1, comprising delivering the oxidative reductive potential water solution in the form of a spray or aerosol.

18. The method of claim 1, comprising delivering the oxidative reductive potential water solution in the form of a mist or steam.

19. The method of claim 1, wherein the oxidative reductive potential water solution comprises from about 20% by volume to about 40% by volume of cathode water.

* * * * *